(12) United States Patent
Griffin et al.

(10) Patent No.: US 10,089,755 B2
(45) Date of Patent: Oct. 2, 2018

(54) GUIDEWIRE DETECTION SYSTEMS, METHODS, AND APPARATUSES

(71) Applicant: LightLab Imaging, Inc., Westford, MA (US)

(72) Inventors: Christopher E. Griffin, Wilton, NH (US); Sonal Ambwani, Westborough, MA (US); Satish Kaveti, Sharon, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 0 days.

(21) Appl. No.: 15/218,871

(22) Filed: Jul. 25, 2016

(65) Prior Publication Data

US 2017/0024910 A1    Jan. 26, 2017

Related U.S. Application Data

(60) Provisional application No. 62/322,693, filed on Apr. 14, 2016, provisional application No. 62/196,997, filed on Jul. 25, 2015.

(51) Int. Cl.
*G06T 11/00* (2006.01)
*A61B 5/00* (2006.01)
(Continued)

(52) U.S. Cl.
CPC ............ *G06T 11/00* (2013.01); *A61B 5/0066* (2013.01); *A61B 5/0084* (2013.01);
(Continued)

(58) Field of Classification Search
USPC .................................................. 382/128, 131
See application file for complete search history.

(56) References Cited

U.S. PATENT DOCUMENTS

| 5,321,501 A | 6/1994 | Swanson et al. |
| 5,459,570 A | 10/1995 | Swanson et al. |

(Continued)

FOREIGN PATENT DOCUMENTS

WO    2012/166332    12/2012

OTHER PUBLICATIONS

Gabriele et al., "Reproducibility of the Carpet View system: a novel technical solution for display and off line analysis of OCT images", Int J Cardiovasc Imaging 30:1225-1233 (2014).
(Continued)

*Primary Examiner* — Ishrat I Sherali
(74) *Attorney, Agent, or Firm* — K&L Gates LLP

(57) ABSTRACT

In part, the disclosure relates to methods of guidewire detection in intravascular data sets such as scan lines, frames, images and combinations thereof. Methods of generating one or more indicia of a guidewire in a representation of blood vessel are also features of the disclosure. A carpet view is generated in one embodiment and regions of relatively higher contrast are detected as candidate guidewire regions. In one embodiment, the disclosure relates to selective removal of guidewire segments from a set of intravascular data and the display of a representation of a blood vessel via a user interface. Representations of a guidewire can be toggled on and off in one embodiment.

23 Claims, 32 Drawing Sheets
(14 of 32 Drawing Sheet(s) Filed in Color)

(51) Int. Cl.
*A61B 8/08* (2006.01)
*A61B 8/12* (2006.01)
*A61M 25/09* (2006.01)
*A61B 5/02* (2006.01)
*A61B 5/06* (2006.01)
*G06T 7/70* (2017.01)
*G06T 7/00* (2017.01)

(52) U.S. Cl.
CPC .......... *A61B 5/02007* (2013.01); *A61B 5/065* (2013.01); *A61B 5/6852* (2013.01); *A61B 5/7217* (2013.01); *A61B 8/0841* (2013.01); *A61B 8/12* (2013.01); *A61B 8/5223* (2013.01); *A61M 25/09* (2013.01); *G06T 7/70* (2017.01); *A61B 8/0891* (2013.01); *G06T 7/0012* (2013.01); *G06T 2207/10101* (2013.01); *G06T 2207/30101* (2013.01)

(56) References Cited

U.S. PATENT DOCUMENTS

| | | | |
|---|---|---|---|
| 5,465,147 | A | 11/1995 | Swanson |
| 5,509,093 | A | 4/1996 | Miller et al. |
| 5,619,368 | A | 4/1997 | Swanson |
| 5,748,598 | A | 5/1998 | Swanson et al. |
| 5,784,352 | A | 7/1998 | Swanson et al. |
| 5,965,355 | A | 9/1999 | Swanson et al. |
| 6,111,645 | A | 8/2000 | Tearney et al. |
| 6,134,003 | A | 10/2000 | Tearney et al. |
| 6,160,826 | A | 12/2000 | Swanson et al. |
| 6,191,862 | B1 | 2/2001 | Swanson et al. |
| 6,282,011 | B1 | 8/2001 | Tearney et al. |
| 6,421,164 | B2 | 7/2002 | Tearney et al. |
| 6,445,939 | B1 | 9/2002 | Swanson et al. |
| 6,485,413 | B1 | 11/2002 | Boppart et al. |
| 6,501,551 | B1 | 12/2002 | Tearney et al. |
| 6,552,796 | B2 | 4/2003 | Magnin et al. |
| 6,564,087 | B1 | 5/2003 | Pitris et al. |
| 6,570,659 | B2 | 5/2003 | Schmitt |
| 6,706,004 | B2 | 3/2004 | Tearney et al. |
| 6,879,851 | B2 | 4/2005 | McNamara et al. |
| 6,891,984 | B2 | 5/2005 | Petersen et al. |
| 7,208,333 | B2 | 4/2007 | Flanders et al. |
| 7,231,243 | B2 | 6/2007 | Tearney et al. |
| 7,241,286 | B2 | 7/2007 | Atlas |
| 7,397,935 | B2 * | 7/2008 | Kimmel .................... G06T 7/11 382/128 |
| 7,414,779 | B2 | 8/2008 | Huber et al. |
| 7,415,049 | B2 | 8/2008 | Flanders et al. |
| 7,625,366 | B2 | 12/2009 | Atlas |
| 7,813,609 | B2 | 10/2010 | Petersen et al. |
| 7,848,791 | B2 | 12/2010 | Schmitt et al. |
| 7,916,387 | B2 | 3/2011 | Schmitt et al. |
| 7,935,060 | B2 | 5/2011 | Schmitt et al. |
| 8,116,605 | B2 | 2/2012 | Petersen et al. |
| 8,206,377 | B2 | 6/2012 | Petroff |
| 8,325,419 | B2 | 12/2012 | Schmitt |
| 8,358,461 | B2 | 1/2013 | Huber et al. |
| 8,412,312 | B2 | 4/2013 | Judell et al. |
| 8,449,468 | B2 | 5/2013 | Petersen et al. |
| 8,478,384 | B2 | 7/2013 | Schmitt et al. |
| 8,478,387 | B2 | 7/2013 | Xu |
| 8,503,844 | B2 | 8/2013 | Petersen et al. |
| 8,581,643 | B1 | 11/2013 | Schmitt |
| 8,582,109 | B1 | 11/2013 | Schmitt |
| 8,582,619 | B2 | 11/2013 | Adler |
| 8,582,934 | B2 | 11/2013 | Adler et al. |
| 8,687,201 | B2 | 4/2014 | Adler |
| 8,786,336 | B1 | 7/2014 | Schmitt |
| 8,831,321 | B1 | 9/2014 | Elbasiony |
| 8,948,228 | B2 | 2/2015 | Adler |
| 8,953,911 | B1 | 2/2015 | Xu et al. |
| 9,138,147 | B2 * | 9/2015 | Schmitt ................ A61B 5/0066 |
| 2002/0161351 | A1 | 10/2002 | Samson et al. |
| 2005/0201662 | A1 | 9/2005 | Petersen et al. |
| 2005/0249391 | A1 * | 11/2005 | Kimmel .................... G06T 7/11 382/128 |
| 2006/0095065 | A1 | 5/2006 | Tanimura et al. |
| 2009/0174931 | A1 | 7/2009 | Huber et al. |
| 2009/0306520 | A1 | 12/2009 | Schmitt et al. |
| 2010/0076320 | A1 | 3/2010 | Petersen et al. |
| 2011/0071404 | A1 | 3/2011 | Schmitt et al. |
| 2011/0101207 | A1 | 5/2011 | Schmitt |
| 2011/0157686 | A1 | 6/2011 | Huber et al. |
| 2011/0190586 | A1 | 8/2011 | Kemp |
| 2011/0228280 | A1 | 9/2011 | Schmitt et al. |
| 2012/0310081 | A1 | 6/2012 | Adler et al. |
| 2012/0238869 | A1 | 9/2012 | Schmitt et al. |
| 2012/0250028 | A1 | 10/2012 | Schmitt et al. |
| 2013/0010303 | A1 | 1/2013 | Petersen et al. |
| 2013/0012811 | A1 | 1/2013 | Schmitt et al. |
| 2013/0023761 | A1 | 1/2013 | Petroff |
| 2013/0051728 | A1 | 2/2013 | Petroff |
| 2013/0072805 | A1 | 3/2013 | Schmitt et al. |
| 2013/0310698 | A1 | 11/2013 | Judell et al. |
| 2014/0018669 | A1 | 1/2014 | Xu |
| 2014/0024931 | A1 | 1/2014 | Winston et al. |
| 2014/0094697 | A1 | 4/2014 | Petroff et al. |
| 2014/0114182 | A1 | 4/2014 | Petersen et al. |
| 2014/0142427 | A1 | 5/2014 | Petroff |
| 2014/0142432 | A1 | 5/2014 | Hutchins et al. |
| 2014/0142436 | A1 | 5/2014 | Hutchins et al. |
| 2014/0187929 | A1 | 7/2014 | Schmitt et al. |
| 2014/0218742 | A1 | 8/2014 | Adler |
| 2014/0249407 | A1 | 9/2014 | Adler et al. |
| 2014/0268167 | A1 | 9/2014 | Friedman et al. |
| 2014/0276011 | A1 | 9/2014 | Schmitt et al. |
| 2014/0309536 | A1 | 10/2014 | Douk et al. |
| 2014/0379269 | A1 | 12/2014 | Schmitt |
| 2015/0153157 | A1 | 6/2015 | Schmitt et al. |
| 2015/0119707 | A1 | 7/2015 | Schmitt |
| 2015/0192405 | A1 | 7/2015 | Schmitt |
| 2015/0257850 | A1 * | 9/2015 | Sakamoto ................ A61B 8/12 600/424 |
| 2017/0148161 | A1 * | 5/2017 | Griffin ................ A61B 5/0066 |

OTHER PUBLICATIONS

International Search Report and Written Opinion for International application No. PCT/US2016/043912 mailed from the International Searching Authority dated Oct. 24, 2016 (11 pages).

* cited by examiner

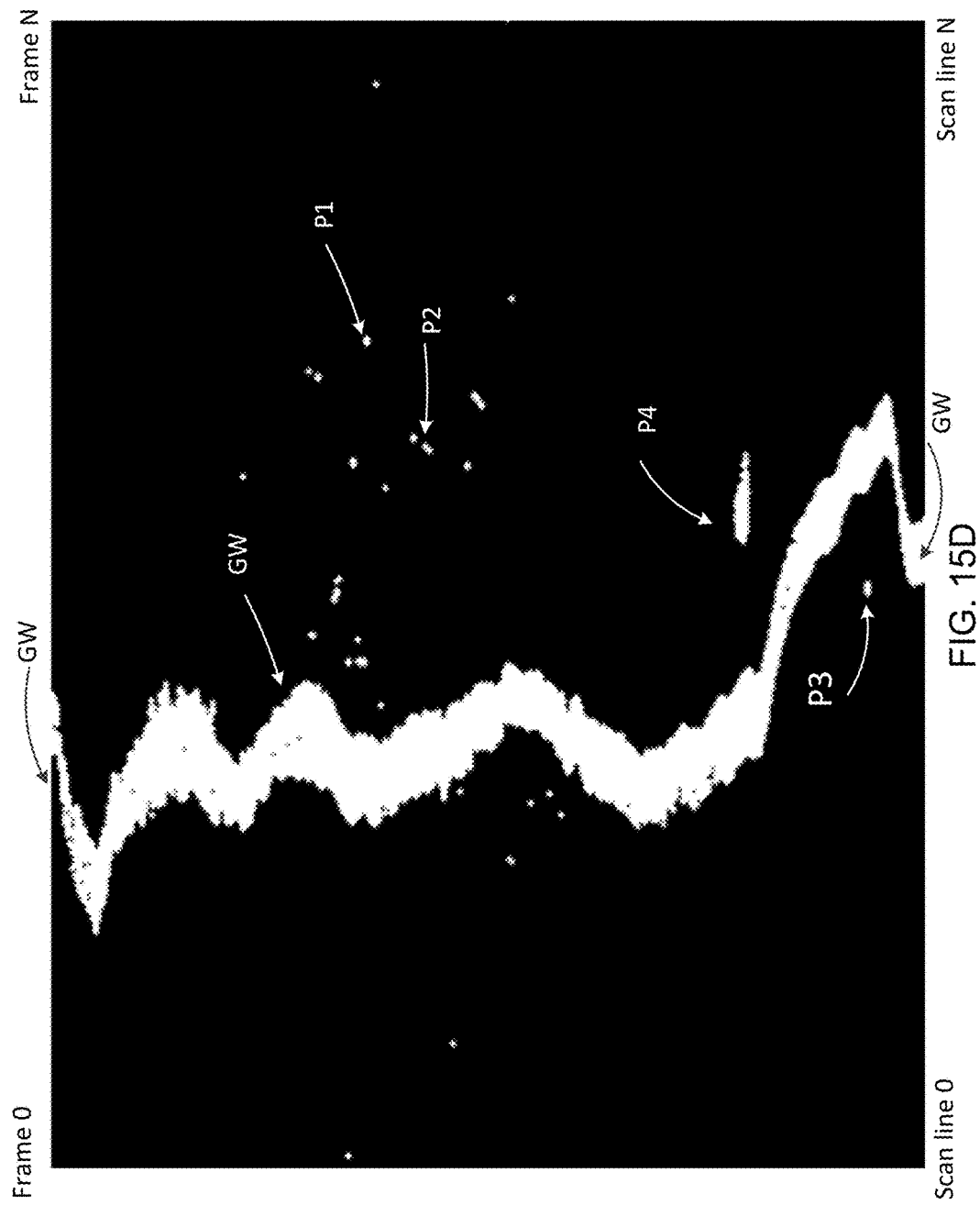

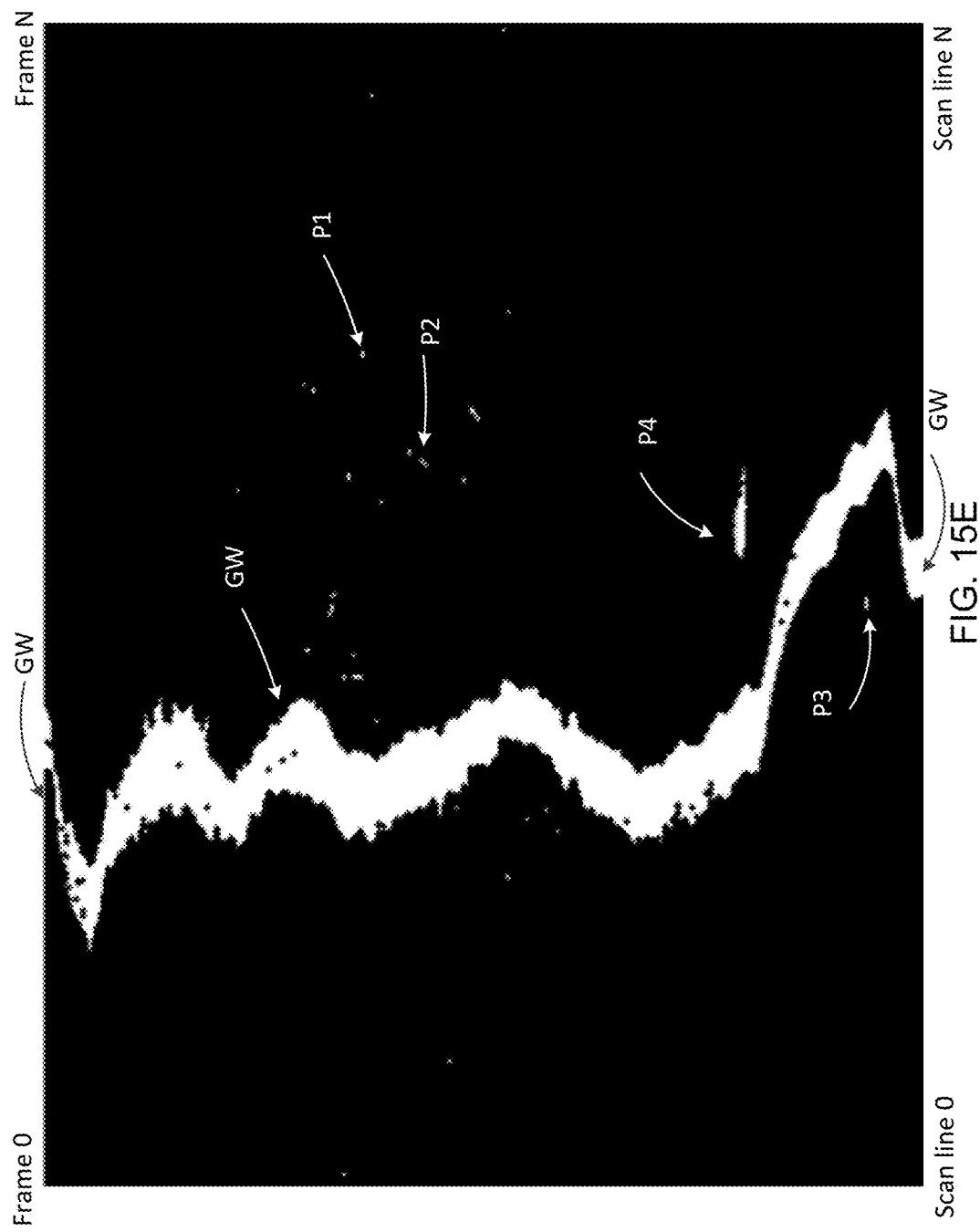

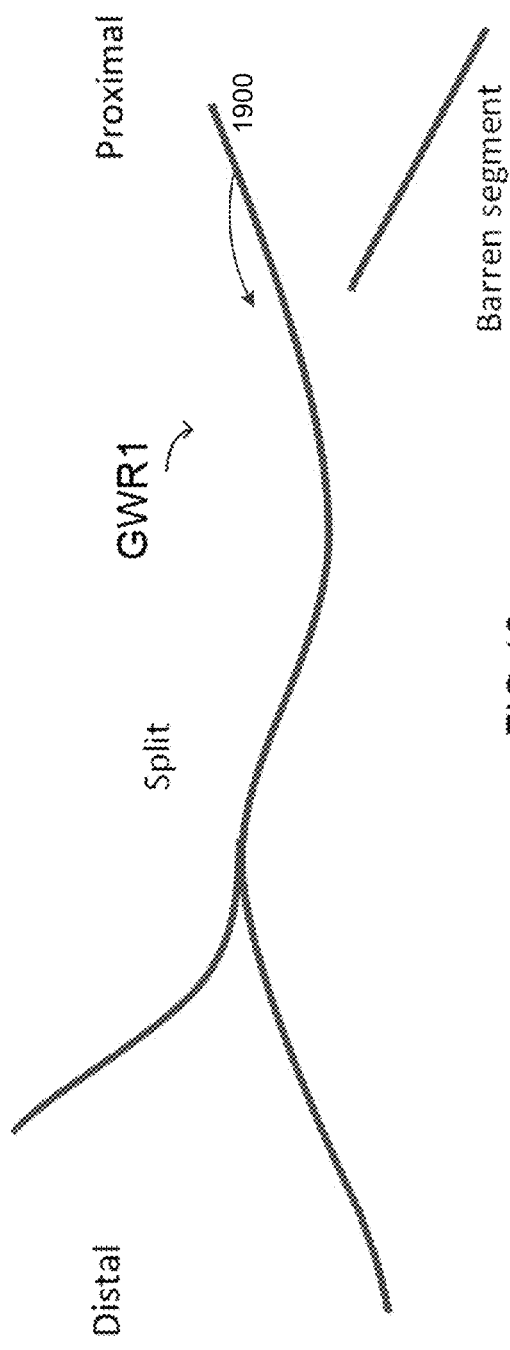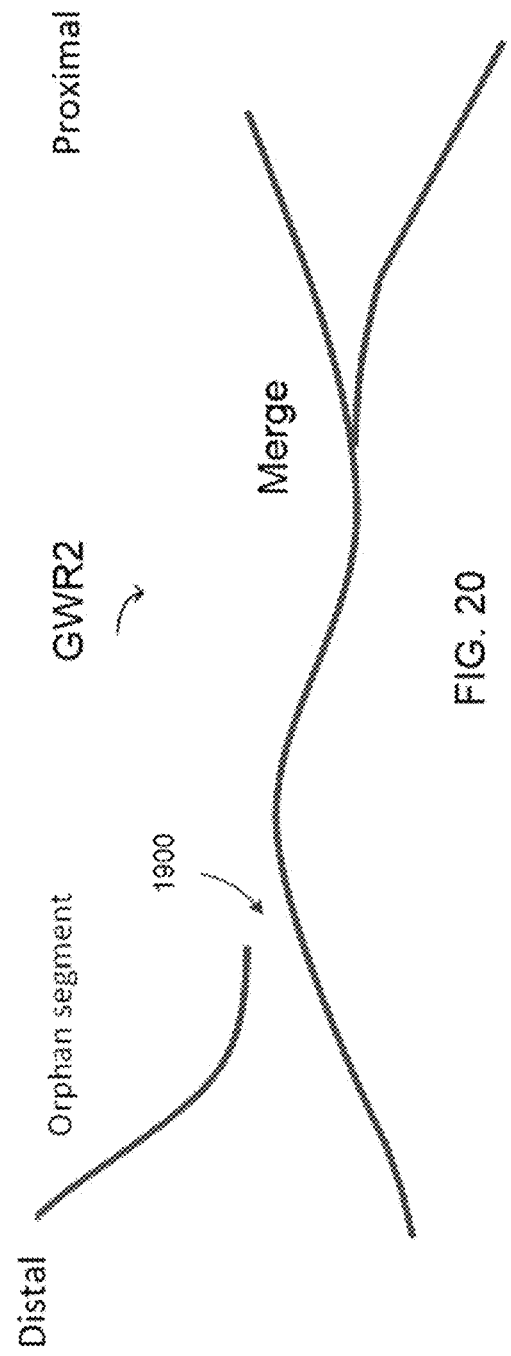
FIG. 19
FIG. 20

GUIDEWIRE DETECTION SYSTEMS, METHODS, AND APPARATUSES

CROSS REFERENCE TO RELATED APPLICATIONS

This application claims the benefit of priority under 35 U.S.C. 119(e) from U.S. Provisional Application No. 62/196,997 filed on Jul. 25, 2015, and U.S. Provisional Application No. 62/322,693 filed on Apr. 14, 2016, the disclosures of which are herein incorporated by reference in their entirety.

FIELD

The disclosure relates generally to the field of vascular system imaging and data collection systems and methods. In particular, the disclosure relates to methods of detecting a guidewire in a blood vessel.

BACKGROUND

Coronary artery disease is one of the leading causes of death worldwide. The ability to better diagnose, monitor, and treat coronary artery diseases can be of life saving importance. Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution.

Viewing subsurface structures with high resolution using fiber-optic probes makes OCT especially useful for minimally invasive imaging of internal tissues and organs. This level of detail made possible with OCT allows a clinician to diagnose as well as monitor the progression of coronary artery disease. OCT images provide high-resolution visualization of coronary artery morphology and can be used alone or in combination with other information such as angiography data and other sources of subject data to aid in diagnosis and planning such as stent delivery planning. In addition to OCT, various optical, acoustic, and other intravascular data collection proves can be used.

Imaging portions of a patient's artery provides a useful diagnostic tool for doctors and others. OCT, ultrasound and other data collection modalities use guide catheters to position a probe in a blood vessel prior to collecting data. One or more guidewires can be used to navigate the tortuous path through the arteries to arrive at a location of interest for data collection. Unfortunately, a guidewire can generate shadows during the process of probe-based data collection. These shadows can negatively affect the imaging of stents and other arterial elements. Accordingly, a need therefore exists to detect the location of a guidewire and develop methods of representing it and using it to inform the detection of other intravascular elements. The present disclosure addresses this need and others.

SUMMARY OF THE INVENTION

In part, the disclosure relates to methods that deal with the complexities associated with detecting a guidewire in the presence of an imaging probe, stents, and other intravascular features. The methods and implementations described herein can be used with various intravascular imaging systems and probes.

In part, the disclosure relates to operations and methods performed upon diagnostic data such as intravascular data generated using a diagnostic system. Examples of such a system can include an optical coherence tomography, an intravascular ultrasound imaging and other data intravascular data collection systems. The methods and systems described herein can use various steps and processing stages to detect a guidewire in a blood vessel. In various embodiments, the systems and methods display a representation of the guidewire relative to a representation of a lumen of a blood vessel. This display can be in one or more user interface panels and include two or three-dimensional representations.

One embodiment of the disclosure relates to methods of guidewire detection. The method can include various steps stages as described herein. In one embodiment, the method includes generating one or more indicia relative to a representation of a blood vessel corresponding to the guidewire. A carpet view is generated in one embodiment and regions of relatively higher contrast are detected as candidate guidewire regions. The method can also include identifying guidewire segments that make up a given guidewire. In one embodiment, the method includes removal of guidewire segments and guidewires from a display of a representation of a blood vessel via a user interface.

In one embodiment, the disclosure relates to performing guidewire detection as an intermediate step in a pipeline of software modules, operators and stages that transform intravascular data and perform feature detection such as shadow and lumen detection thereon. For example, guidewire detection can be performed after an OCT or IVUS pullback and the resulting intravascular data can be processed using a lumen detection software module to extract lumen data such as information relating to a lumen boundary. Various shadows can be detected in the dataset. In addition, identified shadows can be further evaluated to validate them as shadows associated with a guidewire segment. In turn, once guidewires have been identified and validated within the intravascular data, this information can be provided to other intravascular data processing modules. As an example, validated guidewire detections can be an input to a side branch detection module.

In one embodiment, the method of guidewire detection can include generating one or more binary masks of one or more frames of intravascular data. The binary mask can be cleaned such as by denoising or filtering using binary morphology. The process of detecting offsets can be performed relative to the mask or other intravascular images. In one embodiment, guidewire detection can be facilitated, in part, by using one or more carpet view based approaches. Once a carpet view has been obtained further processing operations can be performed relative thereto such as by generating a binary mask of the carpet view.

In one embodiment, the binary carpet view mask of the intravascular data can be used to validate candidate guidewire detections in one embodiment. In one embodiment, the carpet view mask, a binary mask, is used as an input for subsequent intravascular image processing stages in which invalid detections of guidewire segments are eliminated. In one embodiment, the thickness of the guidewire generating the shadow has a thickness that ranges from about 20 microns to about 60 microns. In one embodiment, the method includes the steps of processing of carpet view image to generate carpet view mask; generating a set of guidewire segments; removing spurious segments; linking of detections to form segments and establishing parent/child relationship between segments; linking of segments to create wires; removing duplicate wires; and post processing.

The invention relates, in part, to a method of detecting a guidewire in a blood vessel. The method can include storing, using an intravascular imaging system, one or more intravascular image datasets of the blood vessel, each intravascular dataset comprising a plurality of scan lines; detecting a guidewire shadow on one or more scan lines of the plurality of scan lines; determining a guidewire offset for each guidewire shadow; determining on a per frame basis a candidate guidewire detection using one or more guidewire offsets such that a plurality of candidate guidewire detections is generated; generating a plurality of candidate guidewire segments from the plurality of candidate guidewire detections; removing spurious guidewire segments from the plurality of candidate guidewire segments to generate a set of detected guidewire segments; and linking segments from the set of detected guidewire segments to generate one or more contiguous guidewire representations.

The method can include displaying a guidewire representation comprising one or more contiguous guidewire representations in a user interface of the intravascular imaging system.

The method can include generating a carpet view from the plurality of scan lines; and binarizing the carpet view to generate a binary carpet view mask; wherein the step of removing spurious guidewire segments includes scoring candidate guidewire segments based on intersection of the candidate segments with "on" regions in the binary carpet view mask. ON or "on" regions can also be replaced with OFF or "off" regions. Further, in lieu of ON/"on" or OFF/"off" any other binary states can be used and the values can be swapped such that OFF is used for ON, and vice versa for a given binary state representation.

The method can include generating a mapping of all possible detection linkages from the plurality of candidate guidewire detections, and using the segment mapping to link the detections into contiguous guidewire representations.

The method can include detecting a guidewire shadow on one or more scan lines of the plurality of scan lines; determining a guidewire offset for each guidewire shadow; and determining on a per frame basis a candidate guidewire detection is performed using a single-frame processing implementation.

The method can include generating a plurality of candidate guidewire segments; removing spurious guidewire segments; and forming guidewire representations from the set of detected guidewire segments are performed using a multi-frame processing implementation.

The segment linking can include linking a detection from a distal frame to an existing segment if a distance metric between a tail of the segment and a new detection is less than a threshold; and linking a detection from a next most distal frame to an existing segment if an extrapolated location of that segment within the frame lies within a narrow distance of the detection.

The method can include providing interpolated detections when segments are linked to detections that lie on frames crossing over one or more frames on which there are no detection. The segments can be filtered using a set of exclusion rules to remove segments that have probability of less than about 0.5 of corresponding to an actual guidewire. The distinct segments can be bounded by one or more of a split and a merge in which a parent segment is linked to two child segments (for a split) or two parents connect to a single child segment (for a merge).

Segments can be linked based upon occurrence of one or more conditions selected from the group consisting of: each unique segment has at least one corresponding wire associated with it; when a segments splits in two, a new wire is created; when segments merge, a resulting segment is associated with multiple wires associated with the parent segments; duplicate wires are eliminated after linking; and wires travelling along common segments are disambiguated for visualization purposes by translating detections on common segments away from each other so that rendered guidewires do not overlap in 3-D space.

The invention also provides, in part, a programmable processor-based computing device of an intravascular imaging system for detecting one or more guidewires in a blood vessel. The programmable processor-based computing device can include one or more data access channels to receive intravascular imaging data; a processor and associated memory in electrical communication with the one or more data access channels. The processor can be programmed to: store, using an intravascular imaging system, one or more intravascular image datasets of the blood vessel, each intravascular dataset comprising a plurality of scan lines; detect a guidewire shadow on one or more scan lines of the plurality of scan lines; determine a guidewire offset for each guidewire shadow; determine on a per frame basis a candidate guidewire detection using one or more guidewire offsets such that a plurality of candidate guidewire detections is generated; generate a plurality of candidate guidewire segments from the plurality of candidate guidewire detections; remove spurious guidewire segments from the plurality of candidate guidewire segments to generate a set of detected guidewire segments; and link segments from the set of detected guidewire segments to generate one or more contiguous guidewire representations.

The programmable processor-based computing device can include one or more of the following features. The processor can be programmed to display a guidewire representation comprising one or more contiguous guidewire representations in a user interface of the intravascular imaging system.

The processor can be programmed to generate a carpet view from the plurality of scan lines; and binarize the carpet view to generate a binary carpet view mask; wherein the step of removing spurious guidewire segments includes scoring candidate guidewire segments based on intersection of the candidate segments with "on" regions in the binary carpet view mask.

The programmable processor-based computing device wherein the processor is further programmed to generate a mapping of all possible detection linkages from the plurality of candidate guidewire detections, and using the segment mapping to link the detections into contiguous guidewire representations.

The processor can be programmed to detect a guidewire shadow on one or more scan lines of the plurality of scan lines; determine a guidewire offset for each guidewire shadow; and determine on a per frame basis a candidate guidewire detection is performed using a single-frame processing instructions.

In the programmable processor-based computing device one or more of: generating a plurality of candidate guidewire segments; removing spurious guidewire segments; and forming guidewire representations from the set of detected guidewire segments, are performed using a multi-frame processing implementation.

Segment linking can include linking a detection from a distal frame to an existing segment if a distance metric between a tail of the segment and a new detection is less than a threshold; and linking a detection from a next most distal frame to an existing segment if an extrapolated location of that segment within the frame lies within a narrow distance of the detection.

The processor can be programmed to provide interpolated detections when segments are linked to detections that lie on frames crossing over one or more frames on which there are no detection. Segments can be filtered using a set of exclusion rules to remove segments that have probability of less than about 0.5 of corresponding to an actual guidewire. Distinct segments can be bounded by one or more of a split and a merge in which a parent segment is linked to two child segments (for a split) or two parents connect to a single child segment (for a merge).

Segments can be linked based upon occurrence of one or more conditions selected from the group consisting of: each unique segment has at least one corresponding wire associated with it; when a segments splits in two, a new wire is created; when segments merge, a resulting segment is associated with multiple wires associated with the parent segments; duplicate wires are eliminated after linking; and wires travelling along common segments are disambiguated for visualization purposes by translating the detections on the common segments away from each other so that rendered guidewires do not overlap in 3-D space.

In one embodiment, the disclosure relates to a non-transitory machine-readable memory medium encoded with a plurality of processor-executable instructions to perform a method of detecting a guidewire in a blood vessel, comprising processor instructions to perform one or more of the steps described and depicted herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The figures are not necessarily to scale; emphasis instead generally being placed upon illustrative principles. The figures are to be considered illustrative in all aspects and are not intended to limit the invention, the scope of which is defined only by the claims.

FIG. 15C-15G are exemplary images after the application of various image processing steps on the carpet of view of FIG. 15B according to an illustrative embodiment of the disclosure.

FIG. 19 is a schematic diagram of guidewire segments showing linking of segments at a split with a barren segment according to an illustrative embodiment of the disclosure.

FIG. 20 is a schematic diagram of guidewire segments showing linking of segments at a merge with orphan segments according to an illustrative embodiment of the disclosure.

DETAILED DESCRIPTION

The systems and methods disclosed herein relate to intravascular imaging and feature detection of guidewires and shadows associated therewith disposed in a blood vessel such as an artery. A given blood vessel can include a delivery catheter that includes wire braiding, previously deployed stents, and other features which generate shadows which can present challenges when imaging an artery. The disclosure also relates to the display and representation of guidewires in two-dimensional and three-dimensional representations as part of a user interface for a diagnostic system. The presence of guidewire segments and their associated shadows in an intravascular region are problematic because they can be misidentified as a stent strut, side branch, stenosis, lipid pool or otherwise obscure a feature of interest during a diagnostic procedure. A guidewire shadow can also obscure a region of interest to an end user. As such, determining and distinguishing shadow locations is useful because it improves diagnostic activities such as evaluating stenosis and stent deployment planning.

A guidewire and its associated shadow in intravascular images such as OCT and IVUS images can cause unwanted image processing errors and interfere with other steps in an image processing pipeline. The fact that some intravascular procedures can include two or more guidewires adds further complexity when attempting to deal with shadows they create as well identify their overlaps, branches and mergers in an arterial image. Also, accurate shadow detection is a predicate step for side branch and stent strut detection in one embodiment. As a result, given the guidewire location in intravascular images can affect the accuracy of results shown to an end user and other related imaging processing modules, accurate guidewire detection and representations (or removals) thereof are of diagnostic significance.

In part, the disclosure relates to guidewire detection methods and various systems, implementations and related processes and subprocesses or stages thereof. The method can be implemented using a pipeline of software module that operates upon datasets generated from an intravascular imaging probe. The methods and software modules are used to perform the various guidewire detection related operations and steps or otherwise use the outputs of a guidewire detection workflow to perform other detection or display processes such as side branch or stent detection.

Various guidewire detection methods and software implementations can be used with a diagnostic system such as data collection system of FIG. 1 described in more detail below. The software modules and associated methods and steps described and illustrated herein are used to perform the various guidewire related steps and operations. Detection of guidewire shadows can be performed using one or more software modules and related steps to determine a location of the shadow cast by the guidewire onto the lumen.

Figure 1:
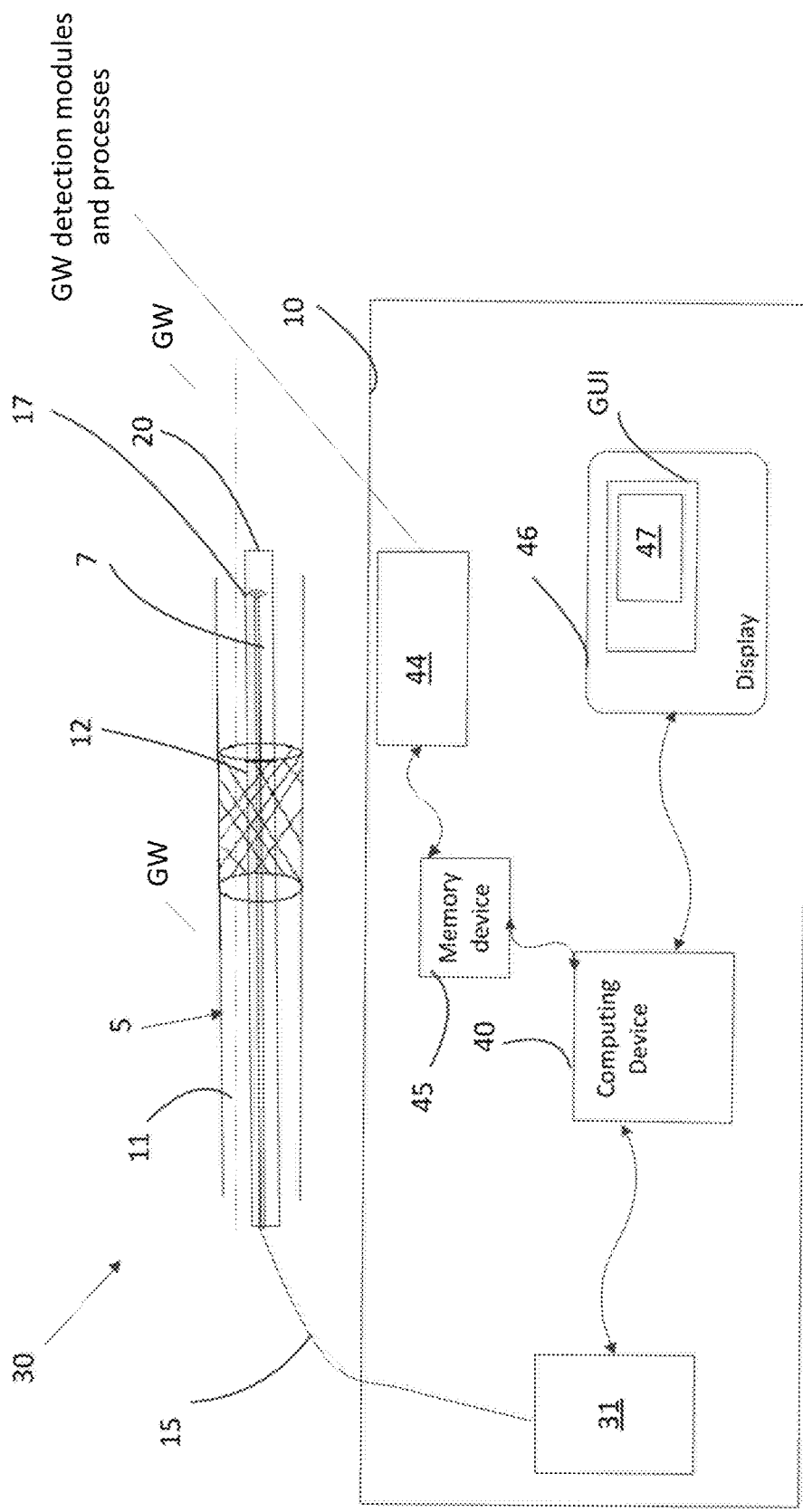
FIG. 1 is an exemplary intravascular data collection system and an associated intravascular data collection probe and related image processing, detection, and other software components according to an illustrative embodiment of the disclosure.
Figure 2:
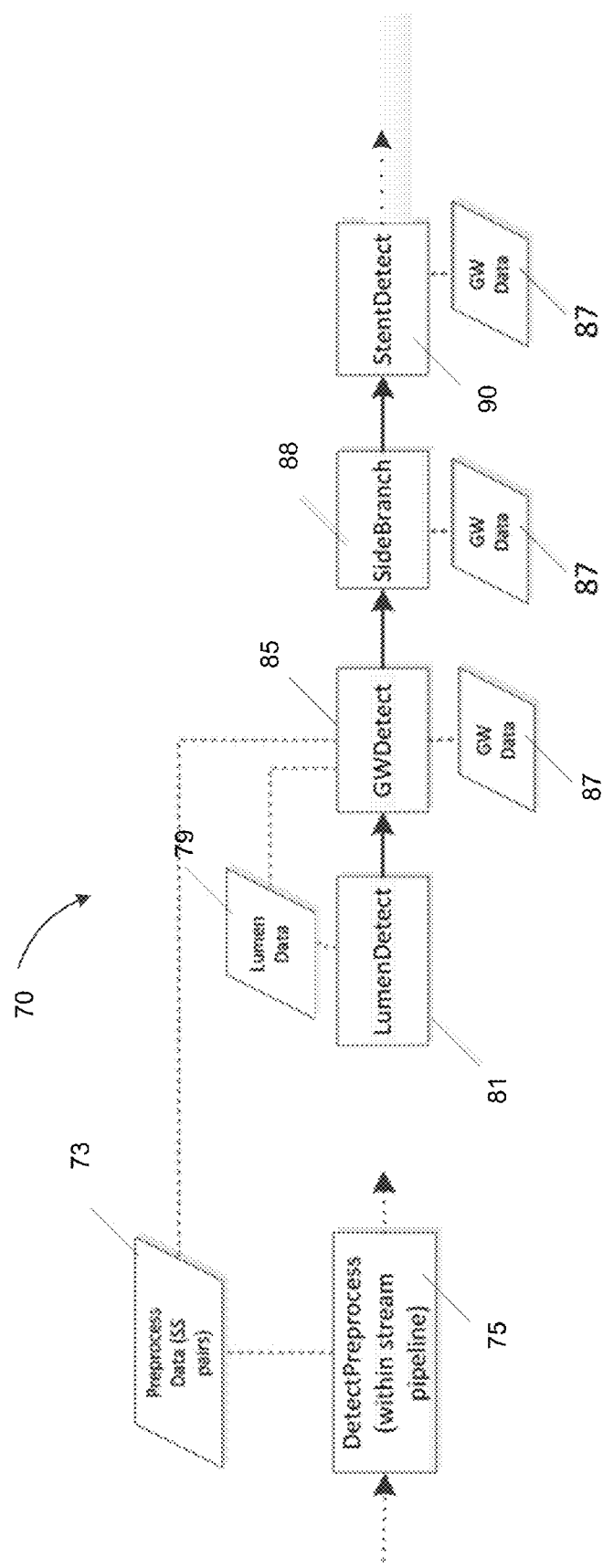
FIG. 2 is an exemplary pipeline of intravascular data processing software modules according to an illustrative embodiment of the disclosure.

Computation of guidewire offset can also be performed by one or more software modules used in conjunction with the system of FIG. 1 and the exemplary data pipeline of FIG. 2. The offset of the guidewire within the shadow region is computed by searching for peaks, transitions, or relative extrema along the scan lines within the shadows. Interpolate to model connected wires can also be performed using one or more modules and various intravascular data processing steps. This interpolation step constructs a segment of guidewire detections in a frame and connects valid segments to create a connected model of the guidewires. A segment can be determined to be valid based on various criteria which can be used to score segments. Segments scores and segment continuity can be used to generate guidewires. A guidewire can be scored based on its segments. To give further context, a discussion of a diagnostic system for performing methods of the disclosure is described in FIG. 1.

FIG. 1 is a high level schematic diagram depicting a blood vessel 5, such as an artery, a data collection probe 7 and an intravascular data collection and processing system 10. A guidewire GW is shown in the blood vessel 5. The system 10 can include for example, an OCT, IVUS, or other intravascular imaging system. A stent 12 is shown in the blood vessel 5. Shadows from the guidewire within the stent can causes stent detection errors and otherwise interfere with imaging of the vessel 5.

The stent 12 includes a plurality of struts. Some of the struts can generate shadows or shadow regions SR as part of the process of imaging the vessel with an intravascular probe. The guidewire also generates shadows. In addition, guide catheters and side branches can also generate shadows during image data collection. The system 10 can include various software modules suitable for performing side branch detection, peak detection, shadow region detection and processing, error correction, model comparisons, lumen detection, stent detection, and various other processes as described herein.

The system 10 can include a suitable light source that satisfies the coherence and bandwidth requirements of the applications and data collection described herein. The system 10 can include an ultrasound imaging system. The probe 7 can include a catheter 20 having a catheter portion having one or more optical fibers 15 and a probe tip 17 disposed therein. The probe tip 17 includes a beam director in one embodiment.

As shown, the catheter 20 is introduced into the lumen 11 such as an arterial lumen. The probe 7 can include a rotating or slidable fiber 15 that directs light forward into the lumen 14 or at a direction perpendicular to the longitudinal axis of the fiber 15. As a result, in the case of light that is directed from the side of the probe as the fiber 15 rotates, OCT data is collected with respect to the walls of the blood vessel 5. The walls of the blood vessel 5 define a lumen boundary. This lumen boundary can be detected using the distance measurements obtained from the optical signals collected at the probe tip 17 using lumen detection software component. Shadow regions, guidewires, and other features can be identified in the scan lines generated by the probe during a pullback through the artery. Segments of a guidewire can be imaged and assembled into a continuous guidewire 2D or 3D representation. The probe 7 can include other imaging modalities in addition to OCT such as ultrasound in one embodiment.

As shown in FIG. 1, the probe tip 17 is positioned in the lumen 14 such that it is distal to a stented region of the blood vessel 5. The probe tip 17 is configured to transmit light and receive backscattered light from objects, such as for example stent 12, and the wall of the blood vessel 5. The probe tip 17 and the rest of the data collection probe 7 are pulled through the lumen 14 such that the tip passes through the stented region and image the stent struts and the guidewire GW. These struts and GW can generate shadows when imaged. The probe 7 is in optical communication with an OCT system 10. The OCT system or subsystem 10 that connects to probe tip 17 via an optical fiber 15 can include a light source such as a laser, an interferometer having a sample arm and a reference arm, various optical paths, a clock generator, photodiodes, and other OCT system components.

In one embodiment, an optical receiver 31 such as a balanced photodiode based system can receive light exiting the probe 7. A computing device 40 such as a computer, processor, ASIC or other device can be part of the OCT system 10 or can be included as a separate subsystem in electrical or optical communication with the OCT system 10. The computing device 40 can include memory, storage, buses and other components suitable for processing data and software 44 such as image data processing stages configured for side branch detection, stent strut candidate selection or identification, candidate guidewire detection, offset determination, binary guidewire carpet-view mask creation, pullback data collection and routing and the other guidewire related methods and analysis and display and detection steps described herein. The software modules 44 can include a shadow detection module and associated processes and steps as described herein.

In one embodiment, the computing device 40 includes or accesses software modules or programs 44, such as a GW detection software modules and methods. Additional details on the software of pipeline 44 are described herein such as with regard to FIG. 2. The software modules or programs 44 can include an image data processing pipeline or component modules thereof and one or more graphical user interfaces (GUI). The modules can be subsets of each other and arranged and connected through various inputs, outputs, and data classes.

An exemplary image processing pipeline and components thereof can constitute one or more of the programs 44 as shown in FIG. 2 and the process flows disclosed herewith. The software modules or programs 44 receive image data and transform such image data into two dimensional and three dimensional views of blood vessels and GWs can include lumen detection software module, peak detection, stent detection software module, side branch detection software module, shadow detection module, scan line selection modules, validation module, image operators, and other software modules to perform the steps described herein. The image data processing pipeline, its components software modules and related methods and any of the methods described herein are stored in memory and executed using one or more computing devices such as a processor, device, or other integrated circuit.

As shown, in FIG. 1, a display 46 can also be part of the system 10 for showing information 47 such as cross-sectional and longitudinal views of a blood vessel generated using collected image data. Representations of a stent and a lumen boundary such as OCT or IVUS images thereof can be shown to a user via display 46. Side branch detection, shadow detection and stent detection are performed prior to the display of these features and any coding or tagging with identifying indicia that may be included in the displayed image. This OCT-based information 47 can be displayed using one or more graphic user interface(s) (GUI). The images of FIGS. 14A, 14B, and 22-26 are examples of information 47 that can be displayed and interacted with using a GUI and various input devices.

In addition, this information 47 can include, without limitation, cross-sectional scan data, longitudinal scans, diameter graphs, image masks, stents, areas of malapposition, lumen border, and other images or representations of a blood vessel or the underlying distance measurements obtained using an OCT system and data collection probe. The computing device 40 can also include software or programs 44, which can be stored in one or more memory devices 45, configured to identify shadows and stent struts including struts within shadow regions and other blood vessel features such as indicia such as text, arrows, color coding, highlighting, contour lines, or other suitable human or machine readable indicia.

Once the OCT data is obtained with a probe and stored in memory; it can be processed to generate information 47 such as a cross-sectional, a longitudinal, and/or a three-dimensional view of the blood vessel along the length of the pullback region or a subset thereof. These views can be depicted as part of a user interface as shown in FIGS. 14A, 14B, and 22-26 and as otherwise described herein.

In one embodiment, the disclosure relates to a pipeline or stream pipeline also referred to as an intravascular data processing pipeline. An exemplary software module based pipeline for implementing the various methods described and depicted herein using an intravascular data collection system is shown in FIG. 2. The pipeline can include a plurality of software modules such as for example a guidewire detection module. The components of the pipeline perform image processing and analysis such as operations and processes on intravascular data, such as scan lines. The pipeline reads data from a pullback generated data set stored in an electronic memory device, operates and routes such data to various software modules, and prepares images to display for the graphical interface of the intravascular data collection system. Data relating to the position and size of the guidewire can be routed to a rendering engine to create a three-dimensional wire frame. 2D images can also be generated as shown herein such as shown in FIG. 26.

Referring to FIG. 2, the image detect software module computes the threshold used by binary image or Binary Image processing component. The method can use a binary image generator as a software module to operate on intravascular data such as scan lines or 2D or 3D images. The binary image generator creates a mask image used by different components to compute the lumen boundary. The various software modules downstream of the lumen detection (LumenDetect) 81 are described in more detail herein. In one embodiment, the GW Data 87 can be received as an input and processed by the various image data processing modules—guidewire detection (GWDetect) 85, side branch detection (SideBranch) 88, and stent detection (StentDetect) 90.

In part, the disclosure relates to a guidewire detection software module also referred to herein as a GWD. The GWD is one intravascular image data software module (or method) within a pipeline of one or more intravascular image data software modules. GWD can include various other related software modules and methods for different tasks relative to the overall method. It works in collaboration with other intravascular image data software modules to locate the guidewire. Modules relevant to guidewire detection are enumerated in FIG. 2. The dotted lines indicate module data that is shared between GWD and other modules. In one embodiment, the guidewire detection pre-processing module encodes "on" regions in binary image for use by subsequent methods. Thus, "off" regions corresponding to blood or lumen can be ignored or processed using other pipeline components. In one embodiment, the GWD identifies the location of guidewire within OCT frames. This identification step can include identifying scan lines that include a portion of the guidewire in one embodiment.

The first module in the guidewire detection method is a guidewire detection preprocess software module. It operates on the binary mask created by the binary image generator module. The binary mask includes "on" regions and "off" regions. As part of the preprocess modules operation on the binary mask, it generates start stop pair data. This data can include a run-length encoding of "on" regions in the image binarization. The "on" and "off" regions correspond to a high value and a low value, such as a zero and a one, or vice versa. In this way, the mask is generated to have a binary data representation. The start stop pair data is used by one or more of the intravascular data processing modules of the pipeline. A guidewire software module generates the guidewire data that is used by stent detection software module to avoid searching for struts in the guidewire regions. The guidewire data is also processed by a side branch module. The guidewire data is an input and is used to reduce false positives by excluding guidewire shadows from side branch detection. In this way, detections of guidewire position and the associated shadows helps improve the accuracy of side branch detection.

The architecture of guidewire detection software can be implemented using various relationships, parameters and data structures. The storage of results of guidewire detections or guidewire candidates can be performed using various classes and object representations in computer readable memory. The methods can use various memory and data management and routing software modules to categorize types of intravascular data and guidewire data and manage such data.

Guidewire Data/Location Information

Various intermediate outputs and inputs for the various operators and software modules that are stored in memory. One or more memories, such as a first computer readable memory and a second computer readable memory can be used to store the results of the guidewire detection methods. In one embodiment, guidewire detection implementations can use various data categories and parameters to define all data storage members needed by the algorithm and methods for managing their display. Some exemplary categories of guidewire related data or parameters suitable for use in a given embodiment can include guidewire frame data, location data, tissue offsets, and others as described herein The category or class of guidewire data can include per frame data. The class or category of guidewire data (or guidewire parameters) can include shadow edge, candidate guidewire data, guidewire segments, and others as disclosed herein. In one embodiment, shadow edge data can include the scan line position of edge delimiting the guidewire region. The candidate guidewire data defines a candidate guidewire location and dimensions in one embodiment. Candidate guidewire data can include one or more of offset, shadow width, vertex, frame position, and center position. A guidewire segment can define a connected set of guidewire detections or segments.

The storage of results of guidewire detection class is instantiated in the pipeline and passed to all modules through an intravascular data collection software module. The data used by the image processing pipeline can be of various forms. In one embodiment, the features found in a specific frame, including lumen offsets, vector of shadow edge positions, list of detections and guidewire offsets are stored as one or more vectors, matrixes or lists.

The various components and steps of the GWD can generate a set of guidewire segments as objects stored in a first memory or more memories. In one embodiment, these guidewire segments objects or stored information can include one or more of a list of parent segments, list of child segments, list of associated detections and wires. In one embodiment, the method and associated software-based modules generate a list that includes guidewire data generated by connecting segments, where each segment contains a list of associated per-frame guidewire detections.

The notion of parent and child segment is informative when evaluating guidewire data processing directionally along frames of data from the proximal end of recording to distal. As segments are linked together, whenever there is a split or a merge, the segment is terminated. Multiple new child segments are then created (in case of split) or a single new child segment is created in case of a merge. The segments are related to each other as parent/child where the parent is always proximal to the child segment.

Various relationships and terms can be used to categorize segments for linking and their various relationships. These terms and relationships can vary based on whether a proximal to distal frame processing order is used or other segment processing and analyzing approaches are used. In one embodiment, segments are linked from Distal to Proximal, in this order: N, N−1, N−2, . . . 3, 2, 1. In one embodiment, when a segment S1 at frame K connects to two (or more) segments S2 and S3 at frame K−1, this is a split and S2 and S3 are children of the parent segment S1. In addition, in one embodiment, when multiple segments S1 and S2 at frame K connect to a single segment S3 at frame K−1, this is a merge and S1 and S2 are parents of the child segment S3. Various other terms and segment linking order conditions and constraints can be used in a given embodiment.

In one embodiment, features detected in a specific frame of intravascular data are stored in one or more computer readable memories such as a first memory and a second memory for example. In one embodiment, each feature is identified by a unique frame number. The various sets or groups of plurality of elements such as candidate guidewire detections, segments, and guidewire representations assembled therefrom can all be stored in such a memory and processed using the various computer-based steps described and depicted herein.

The method can store files and create tables, lists, vectors, matrices, and other data storage implementations that contain references to detections belonging to a guidewire segment. A segment can have multiple parent segments and multiple child segments. In one embodiment, each segment of a guidewire has a unique segment identifier or ID. The GW detections associated to this segment ID are stored in one or more data structures in an electronic machine readable and writeable memory device. A set of guidewire data generated by connecting segment objects that are associated with a segment ID is also generated and stored in memory in one embodiment. Each segment can be associated with multiple guidewires. In one embodiment, multiple guidewire segments are linked together to form a guidewire. A given guidewire can be represented by an instance of guidewire data generated by connecting segments objects which contains references to associated segments and detections.

Individual detections are represented by instances of candidate guidewire location and dimensions data which can be stored as objects or parameters in electronic memory storage. In general, a first memory and a second memory and other memory devices and memory locations can be addressed, written, accessed and read that contain guidewire and intravascular measurement related data. Some of the parameters and outputs from performing guidewire detections can include frame number, scan line for center of guidewire shadow region, guidewire offset in pixels, coordinates of the tip of the guidewire in Cartesian coordinates, coordinates of the center of the guidewire in Cartesian coordinates, pointer to segment associated with a detection, and pointer to segment associated with a detection.

The guidewire detect method operates upon and transforms data from the guidewire detection pre-processing module upstream module as shown in FIG. 2. The update to guidewire data takes individual single-frame processing results and uses cross-frame information to refine the detected guidewire locations by removing invalid guidewire locations, and, filling missing locations by interpolation. In one embodiment, one or more guidewire detections are generated from the multi-frame result to identify the detected guidewire location. Initially, guidewire segments are identified using the guidewire detection process. Guidewire segments are then evaluated and grouped to constitute a given guidewire.

The shadow detection methods are processed as part of a separate or parallel process in one embodiment. Guidewire is abbreviated as GW in various instances throughout the disclosure. The shadow detection related sub-methods of an overall GW detection process can include a separable group of methods. These methods identify shadows cast upon the tissue by guidewires. Exemplary details of the shadow detection method are described herein.

The guidewire detection software module or GWD includes one or more processes or methods as outline below. These can be implemented with regard to frames of image data. In addition, the methods can be implemented using single frame processing or multi-frame processing. In a single frame process, image data processing and the application of masks and other detection steps are performed with regard to a single frame of data. In turn, for a multi-frame process, two or more frames of image data are processed. Multi-frame processing is useful for some of the steps described herein because it allows information from adjoining frames or a set of frames to be considered. A multi-frame process is useful for verifying a candidate guidewire detection is a valid. This can result from the detection being aligned or adjacent with other detections. Detections are expected to span multiple frames because of the elongate geometry of the guidewire. One or more of these frame-based processing regimes can be used in a given embodiment.

Figure 15A:
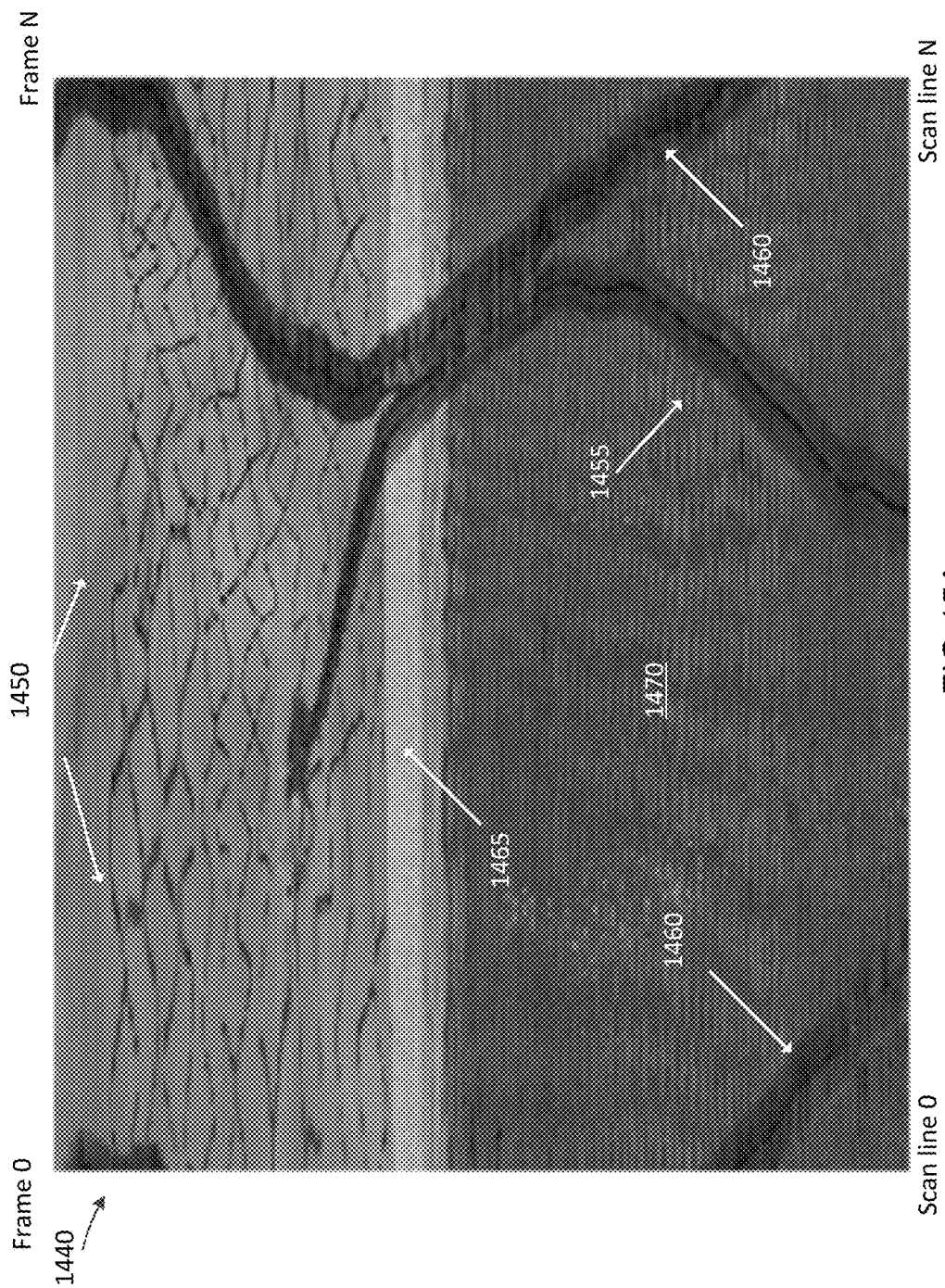
FIG. 15A is an exemplary carpet view image showing guide catheter shadows, stent strut shadows, and guidewire shadows according to an illustrative embodiment of the disclosure.

In one embodiment, the intravascular data is processed using one or more processes part of the data processing pipeline or one or more of the process flows described herein. As part of the guidewire detection processes one or more of the following steps or processes is implemented:
  Shadow region detection (single frame processing)
  Vertex offset detection, wherein the point on the detected guidewire which is closest to the catheter center is referenced as a vertex (single frame processing)
  Creation of carpet view mask which serves as a feature to identify scanlines likely to contain a guidewire
    Carpet view intensity generated in single frame processing
    Morphological processing and binarization of carpet view intensity image occurs in multi-frame processing
  Segment creation, validation and removing invalid segments (multi-frame processing)
  Wire creation by connecting segments and wire selection (multi-frame processing)
  Post-processing of linked wires
  Visualization/display of guidewires These processes or methods can be implemented as software-based methods that operate upon and transform scan lines or other intravascular data from the pullback of probe through an artery. In one embodiment a vertex is referenced as the point on the detected guidewire which is closest to the catheter center. Thus it is aligned on the same scanline and one GW radius closer to the center relative to the center of the detected guidewire. In one embodiment, the post-processing steps include one or more of imaging artifact cleanup, de-duplication of wires (removal of duplicate wires), and disambiguation of overlapping wires. In one embodiment, the guidewire can be displayed or visualized on a display 46. Examples of displayed guidewires identified with regard to data from an OCT pullback are shown in FIG. 15A (carpet view) and FIG. 23A (three-dimensional cut plane view).

Guidewire Shadow Detection Embodiments

Figure 3:
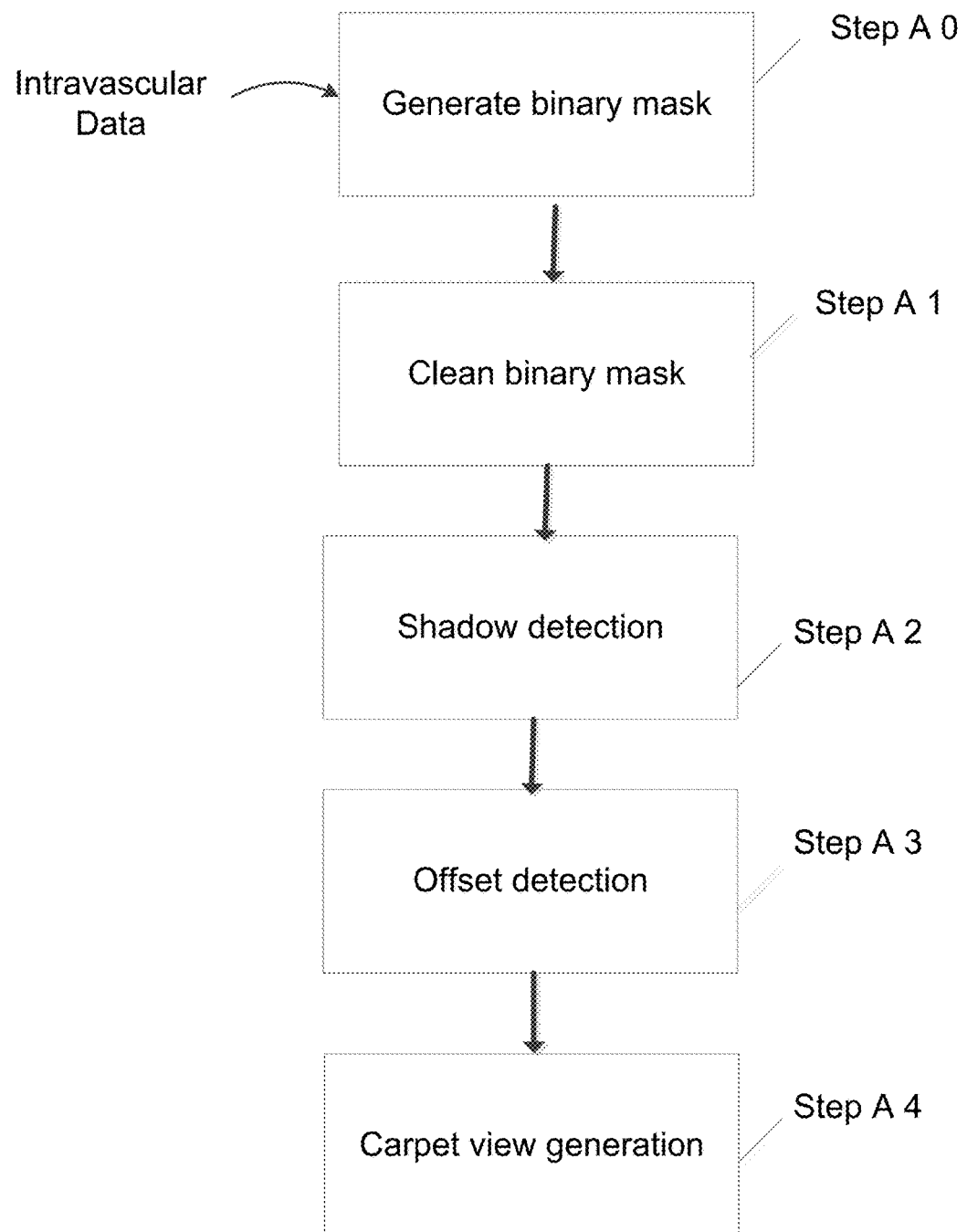
FIG. 3 shows an overview of various initial steps or stages of a guidewire detection process according to an illustrative embodiment of the disclosure.
Figure 4:
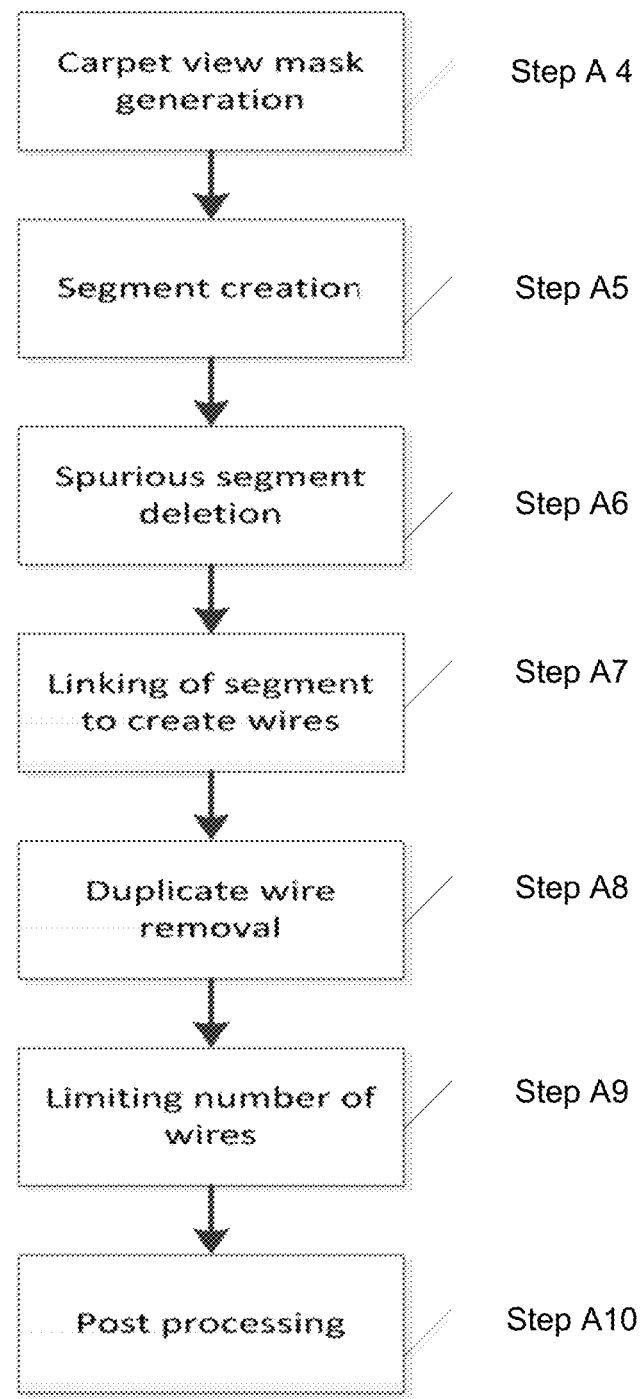
FIG. 4 shows additional steps or stages of a guidewire detection process after a carpet view has been generated according to an illustrative embodiment of the disclosure.

An overview of an exemplary guidewire detection method is summarized in the process flows of FIG. 3 and FIG. 4. FIG. 3 shows single-frame processing features of a guidewire detection process relating to shadows and offsets. In one embodiment, guidewire detection can be facilitated, in part, by using one or more carpet view based approaches. FIGS. 15A-15G and 17 show various details relating to carpet view images and detection and image processing steps applied thereto. FIG. 4 shows a guidewire detection process that uses a carpet view representation generated according to the process of FIG. 3 or otherwise as described herein. In one embodiment, FIG. 3 is implemented using single frame processing. In one embodiment, FIG. 4 is implemented using multi-frame processing.

Introduction to Carpet View

The intravascular image data obtained during a pullback procedure using a probe can be displayed to a user by creating a representation of the scan lines by unfolding a cross-sectional or polar view along a longitudinal view. A carpet view is a two-dimensional data representation. In one embodiment, the carpet view shows a cross-sectional OCT image, but unrolled or unfolded in a manner akin to an unrolled wrapped cylinder of carpet.

The carpet view can be used to conceptualize an OCT image or its underlying components in one or more ways. For example, in one embodiment, the carpet view collapses the radial offset dimension of the 3-D intravascular data set into a single intensity. In this way, the data can be represented in (Z, Theta) coordinates. In one embodiment, the method of collapsing that radial offset dimension is to sum intensity values between a near and far offset estimate. This intensity value summing generates a detectable increase in contrast with respect to certain regions in the carpet view/OCT image. For example, in the carpet this summing process results in a strong detectable contrast whenever in the region of a metallic object that casts a shadow. This contrast, in turn, facilitates detection of such metallic objects such as a guidewire.

In one embodiment, the carpet view or OCT data can be used to generate a binary carpet view mask. The binary carpet view mask of the intravascular data can be generated to facilitate guidewire detection in one embodiment. The process of binarization performed relative to a carpet view image is advantageous. In one embodiment, the carpet view mask, a binary mask, is used as an input for subsequent intravascular image processing stages in which unwanted segments are eliminated.

Figure 17:
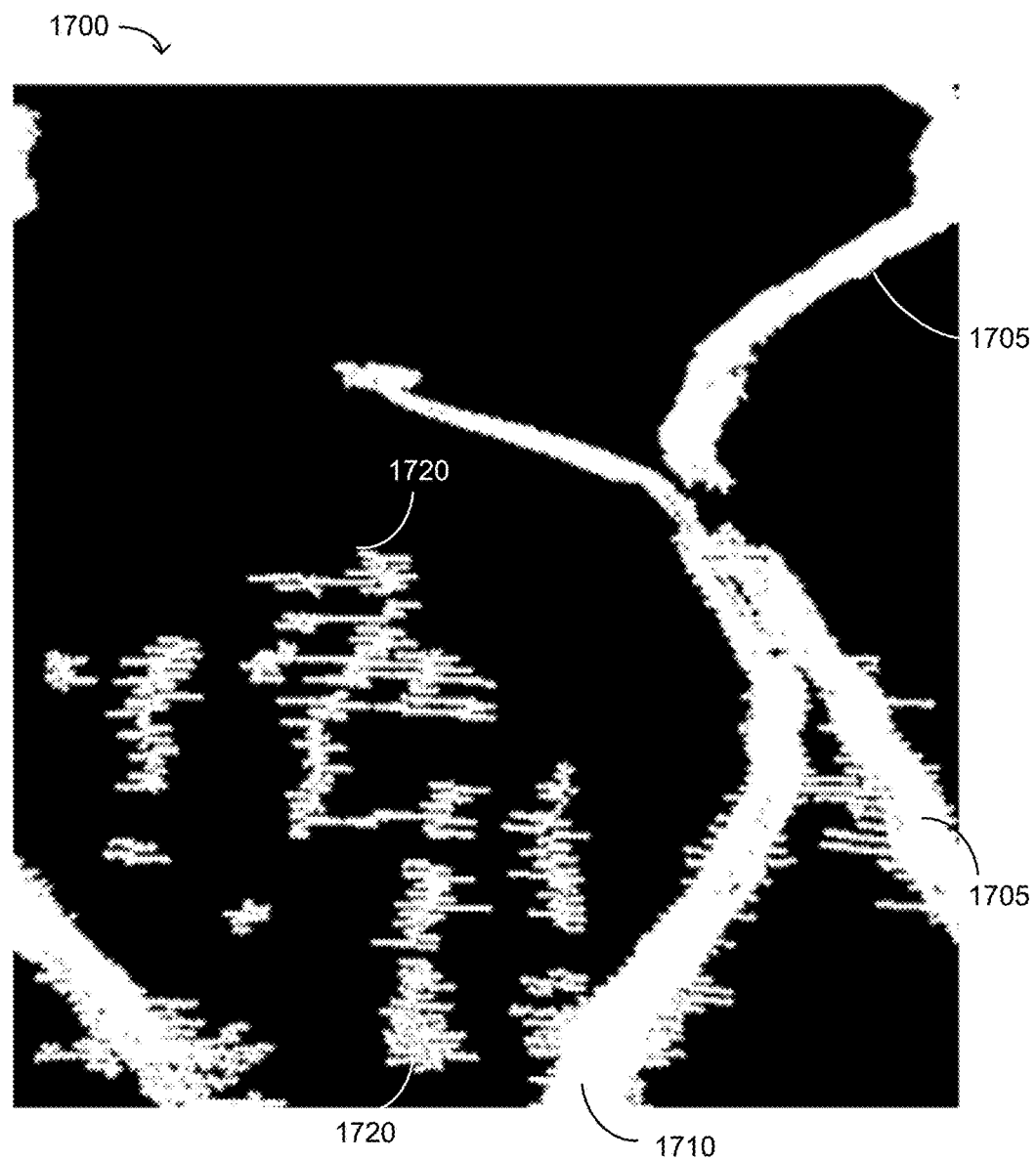
FIG. 17 is a binary mask of a carpet view image showing unwrapped stent struts and guidewire shadows according to an illustrative embodiment of the disclosure.

In one embodiment, the carpet view is a two-dimensional dataset of generated from scan lines of a pullback in which the dimension of the offset along the scan line is removed or reduced. In the carpet view, the intensity values for shadows are low and the intensity values for tissues are high. The carpet view is typically a grayscale image but color versions can be displayed in some embodiment. In FIG. 17, an exemplary carpet view 1700 is shown with two guidewires 1705 and 1710. The intensity values and the connectedness of the guidewire segments are clearly discernable in the carpet view. As a result, the carpet view is an advantages representation of intravascular data when performing guidewire detection steps.

Shadow Region Detection Features

Detection of the shadow region is a step in some embodiments of guidewire detection method. The diagram in FIG. 3 illustrates the shadow region detection method steps. Initially, a binary mask is generated with respect to each frame of image data Step A0. The intravascular data, such as OCT, IVUS, or other image data can be used to generate a binary mask. Additional details relating to binary mask generation can be found in U.S. Pat. No. 9,138,147, the disclosure of which is herein incorporated by reference in its entirety.

In one embodiment, the process of cleaning the binary mask refers to a heuristic method of examining the run-length encoded regions (start-stop pairs) and deciding which runs correspond to the tissue, thereby removing runs corresponding to blood or other artifacts within the lumen. Additional details relating to an embodiment of the process of cleaning the binary mask are described in more detail below.

Figure 5:
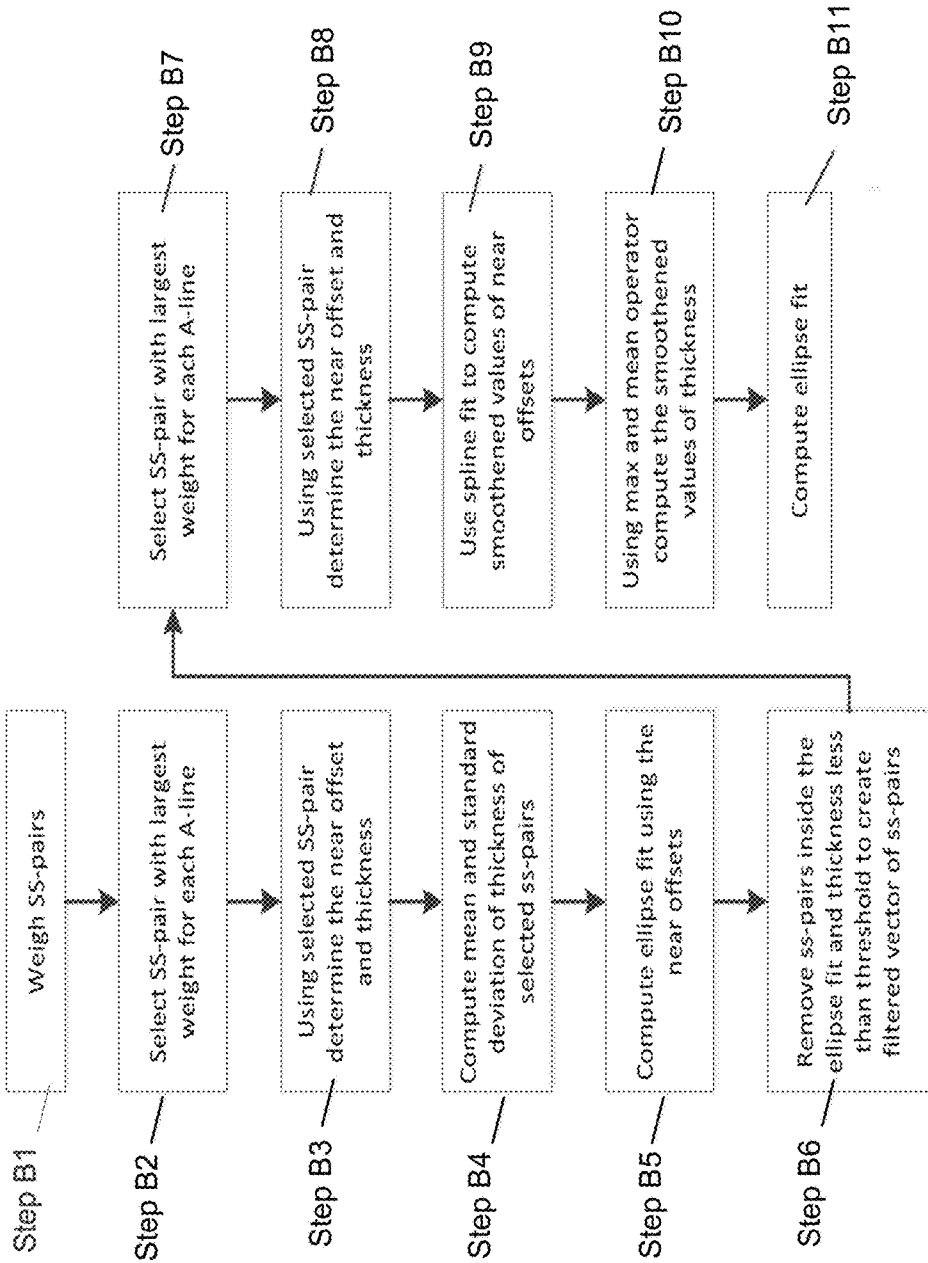
FIG. 5 shows a process flow suitable for identifying start stop pairs for determining offsets and thickness values according to an illustrative embodiment of the disclosure.

FIG. 5 shows a method suitable for identifying start stop pairs for determining offsets and thickness values to direct guidewire search. The method relies in large part on shadow detection to identify the region of interest for guidewire search. In addition to its ordinary meaning, the term offset refers to just one dimension in the 3-D cylindrical coordinate system used for the intravascular data collection via a pullback of a probe through the artery. The term offset refers to the radius measurement from the center of coordinate system to on object of interest, be it a GW, lumen, strut, or something else. Within the context of GW detection, computing the offset means computing the distance from the center of coordinates to the leading edge of the GW. The shortest such distance (the closest point on the GW) is referred to as a vertex in one embodiment.

Thickness is computed as the radial thickness of the binary mask of the detectable tissue signal. As part of guidewire detection, the method uses vectors, lists or other data configurations of one or more types of start-stop pairs such as tissue start stop pairs, generated by the guidewire detection pre-processing module. A start-stop pair (SSPairs) contains start offset, stop offset and thickness in each scan line in a frame. In one embodiment, there are often multiple such SSPairs per scanline. In one embodiment, start stop pairs refer to start and stop of runs of foreground pixels in binary image of the lumen scan lines. In one embodiment, a scan line is a line of image data along a radial line. The term A line can also be used to refer to a scan line in one embodiment.

For each scan line, the start-stop pairs are compared and the one with the largest weight is retained and the corresponding values of start and thickness values are returned in vector offsets and vector thickness parameters respectively. Generally, the method includes weighing the SSPairs Step B1. The weight is computed as follows:

$$\text{weight}=\text{Thickness}*\text{Thickness}+\text{Gap}$$

Figure 6C:
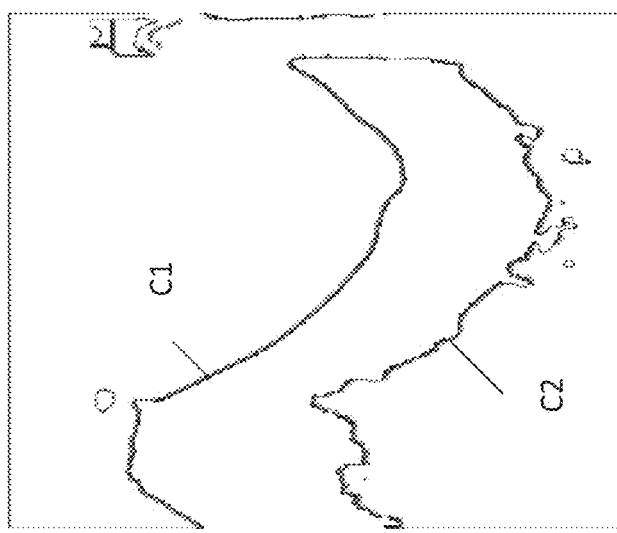
FIGS. 6B and 6C emphasize certain boundaries, offsets and data from the binary mask of FIG. 6A according to an illustrative embodiment of the disclosure.
Figure 6B:
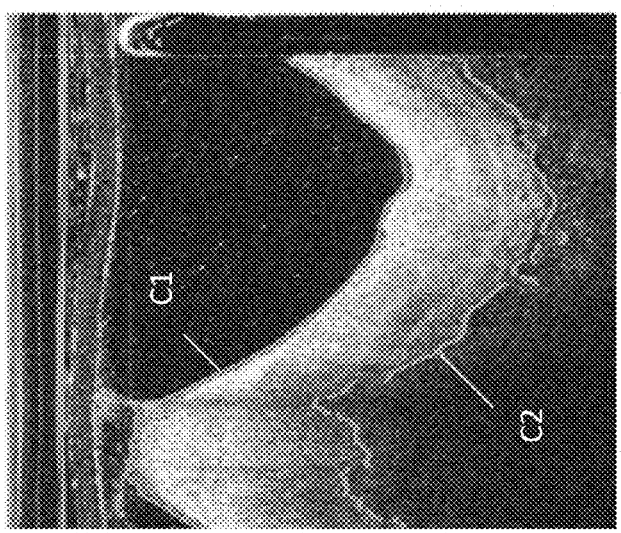
Figure 6A:
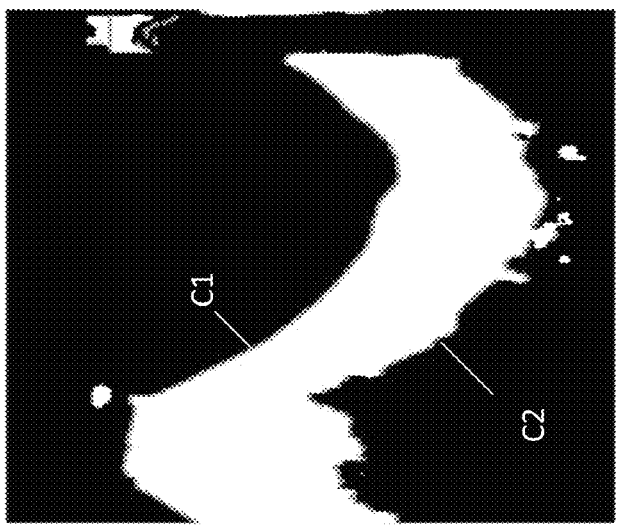
FIG. 6A shows a binary mask of an intravascular image and the associated image along with near and far offset data according to an illustrative embodiment of the disclosure.

The gap can be described as the distance between the start of the current start stop pairs and the stop of the previous start stop pairs. Thickness corresponds to the thickness of the tissue mask. From the computed values of thickness, the method computes the average thickness. The SSPair with the largest weight for each A-line is selected in one embodiment Step B2. The near and far offsets are determined Step B3. It also computes the standard deviation of thickness ($\sigma_d$) Step B4. FIG. 6A illustrates the offsets and thickness of the tissue mask on a binary mask image. Specifically, FIG. 6A shows a lumen offset and thickness profile. FIG. 6B shows the polar image used to generate mask in FIG. 6A. FIG. 6C shows the two contours in isolation from the prior two figures.

The top contour C1 corresponds to the offset of the tissue from origin of the imaging system such as for example the intravascular imaging probe disposed in the artery. The bottom contour C2 corresponds to an estimate of depth of penetration such that once you go past the penetration limit everything else is noise. In one embodiment, each of the contours C1 and C2 can be extended into the shadow zones, and one or more regions defined thereby can be analyzed. These one or more regions include both shadows and tissue. When contours are extended across the shadows, then projection of the pixel values across the tissues in the shadow zones is advantageous because it provides high contrast regions for detection relative to tissue zones. Shadow detection can enhance or made possible in light of the contrasting regions. One analyzed or processed such by an integration operator, a high contrast output dataset can be generated which is suitable for shadow detection.

An ellipse fit is computed using near and far offsets Step B5. In one embodiment, an ellipse is fitted to the vector offsets. This fitted ellipse is used by one or more software modules or processing steps to remove a start-stop pair if one or more of the following conditions are met.

Far offset of Start stop pairs is less than the (ellipse-offset+position-tolerance)

(Average thickness−Start stop pairs thickness)>thickness-threshold

Position-tolerance is equal to 0.0 (used to be standard deviation of thickness ($\sigma_d$)). The value of thickness-threshold ranges from about 0.01 $\sigma_d$ to about 2 $\sigma_d$. The foregoing steps result in cleaning/clearing the binary mask Step B6.

The filtered array of start stop pairs is used again to select the start stop pairs with largest weight to compute the updated near offsets and thickness for each scan line Step B7. The values are used to update the values of vector offsets and vector thickness parameters respectively Step B8. The near offsets are used to fit a spline. In turn, the spline fit is used to compute the smoothed values of near offsets (overwritten into vector offsets) Step B9.

Next a local maxima operator is applied to thickness values (window size of 10 to 150 scan lines) Step B10.

Figure 7:
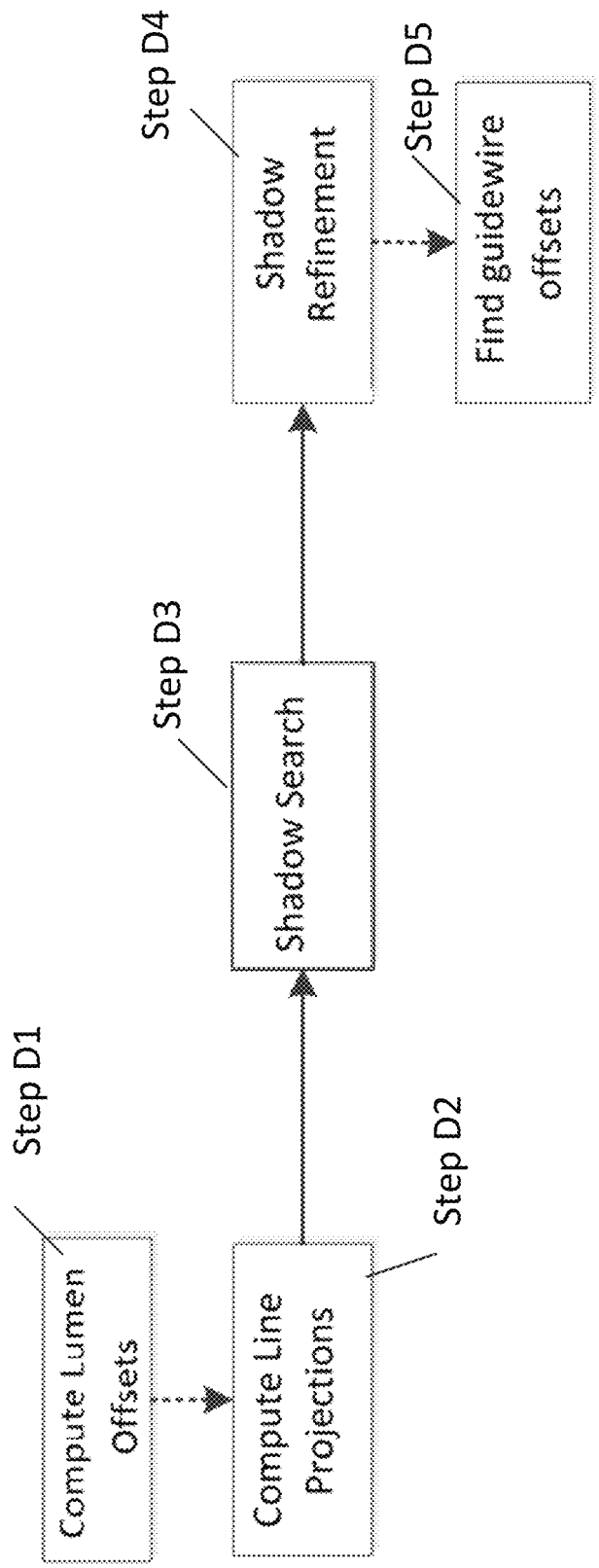
FIG. 7 is a process flow chart of various shadow detection and validation steps and other intravascular data processing steps according to an illustrative embodiment of the disclosure.

Subsequently, an averaging operator is applied (window size 1 to 30 scan lines) to smooth the values of thickness. In addition, in one embodiment, an ellipse fit is obtained again using the near offsets Step B11. The tissue offsets and thickness are computed The next step in the guidewire detection method is the detection of shadows corresponding to the guidewires. FIG. 7 summarizes the steps involved in shadow detection. In one embodiment, these steps include computing lumen offsets Step D1, computing line projections Step D2, performing a shadow search Step D3, performing shadow validation, and performing shadow refinement Step D4 processing relative to initially detected candidate shadows. Additional details relating to these steps are described in more detail below. The first step is to compute line projections. The line projection is searched to determine shadow start-stop locations. The final step is to validate the detected shadows in one embodiment. Using these steps the guidewire offsets can be found Step D5.

Still referring to FIG. 7, the near and far offsets of the tissue mask are used to compute line projections between the near and far points for each scan line. Pixels in line bounded by the near and far offsets are sorted and a percentage of the lower pixel values are averaged. The number of pixels skipped is a function of the total number of pixels and maximum thickness that the intravascular imaging system can resolve with regard to blooming from the guidewire as a result of its reflective nature. The amount of skipped pixels is greater than 1% and less than 20% of the total pixels in one embodiment. The sorting ensures that brightest pixels that may correspond to a strut blooming do not obscure the shadows on the intensity projection. Once the projection for each line is computed, the overall line projection is smoothed with a moving average filter. In one embodiment, a logarithm of the pixel intensities is used for computing the line projection.

Compute Line Projection Method Embodiment

Figure 8:
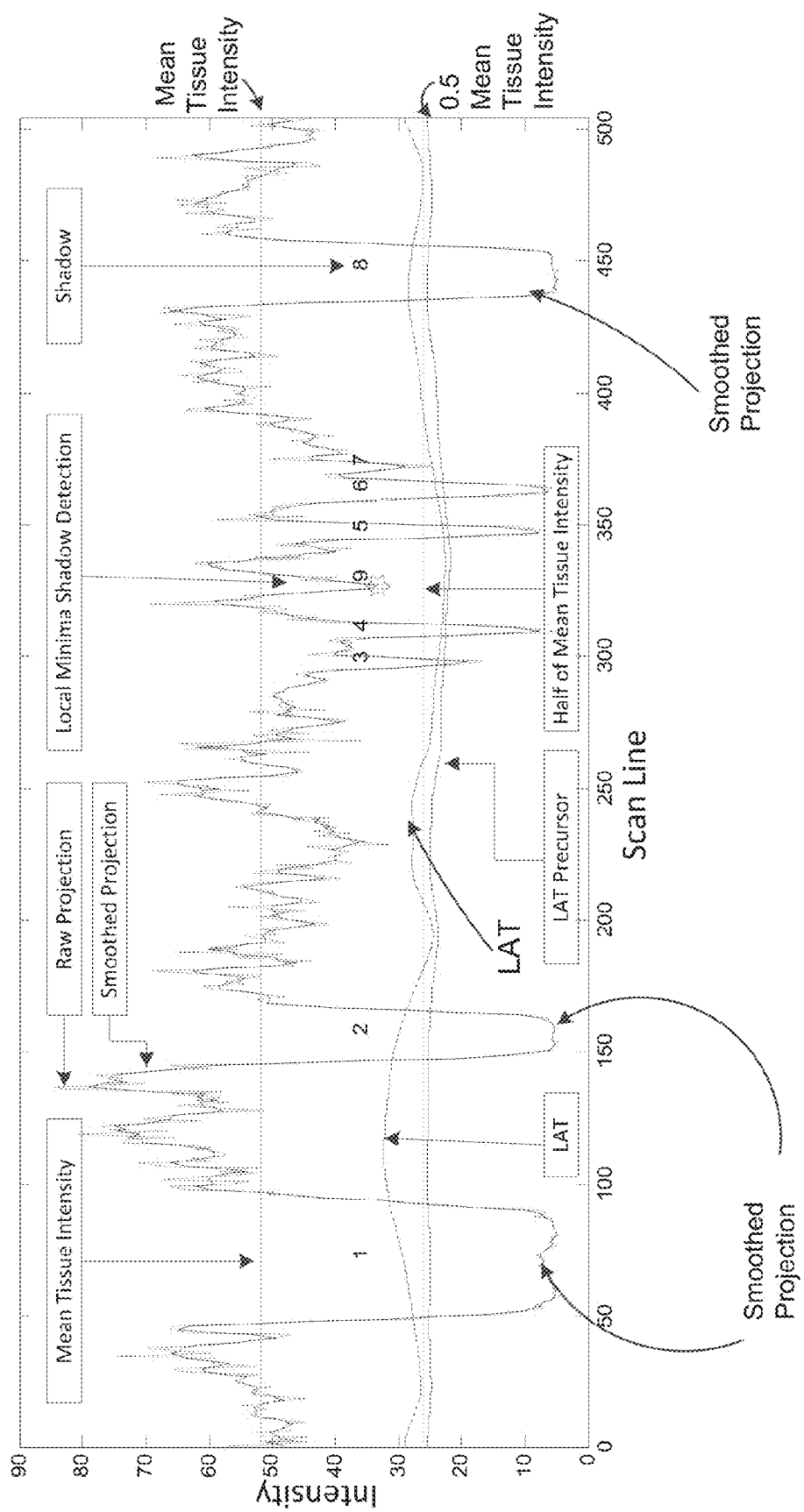
FIG. 8 is a plot of various intravascular data sets and values determined therefrom associated with tissue intensities, projections, relative extrema, locally adaptive thresholds and shadows as curves, lines, or data points in terms of scan lines versus intensity values according to an illustrative embodiment of the disclosure.

FIG. 8 illustrates a typical example of a line projection. Candidate shadows are labeled numerically. The smoothed line projection is marked with the black line (non-smoothed data in green). The subsequent sections describe in further detail the shadow search and validation methods illustrated below. The near and far offsets of binary mask are used to compute line projections between the near and far points for each scan line. In one embodiment, pixels in a line bounded by the near and far offsets are sorted and a percentage of the lower pixel values are averaged. Thus, for each scan line, if all of the pixels are considered in the aggregate an average pixel value can be determined.

A low value relative to that average value (for all pixels) or relative to another average value obtained using a subset of the pixels for a scan line—an average of pixels below a certain intensity threshold can be used to identify a candidate shadow. A fraction of the mean tissue intensity such as 50% of the mean tissue intensity can be used as an intensity floor above which shadows are identified using the LAT-based method. The fraction of the mean tissue intensity used can range from about 20% to about 80% as a floor to select candidate shadows based on valleys in the smoothed line projection of FIG. 8.

A sorting process is performed to increase the probability that the brightest pixels that may correspond to a strut blooming do not obscure the shadows on the intensity projection. Once the projection for each line is computed, the overall line projection is smoothed with a filter such as for example a moving average filter. FIG. 8 illustrates a typical example of a line projection determination. In FIG. 8, data is plotted relative to an intensity axis and a scan line axis as shown. The first horizontal line around intensity level 50 is the mean tissue intensity. The second horizontal line around intensity level 25 is about half of the mean tissue intensity.

In FIG. 8, a smoothed line projection is plotted along with a raw projection and a locally adaptive threshold LAT. The LAT is below the mean tissue intensity and is above and below the half of the mean tissue intensity at different points. The various incidents of shadows correspond to the smooth projection dipping below the LAT curve as shown. The raw projection is jagged and is above or below or overlapping with the smoothed line projection as shown. The mean tissue intensity and half of the mean tissue intensity are also shown in FIG. 8. The LAT is above the LAT precursor as shown.

Candidate shadows are labeled numerically 1 to 9 as shown in FIG. 8. The smoothed line projection is shown relative the raw line projection (non-smoothed data oscillated relative to the smooth data with spikes and jagged points). The star label at point 9 is a genuine shadow the initial operation of the LAT method did not detect. A secondary or backup detection method that uses relative extrema data can be used in parallel with the LAT-based detection method to detect shadows such as those associated with point 9. Point 9 is above the LAT as shown while the other detected shadows 1-8 have projected intensity values below the LAT and thus indicative of being a shadow. Each shadow has a start shadow line.

As an example, a shadow has an approximate start line 150 for shadow 2 and an end shadow line such as approximate line 455 for shadow 8. As shown around scan line 350, the tissue values are lower and thus the LAT is lower relative to the scan line intensity at about scan line 75 as a result the LAT changes based on the scan line and intensity changes in the line projection. In one embodiment, tissue intensity values local to the scan line are used to compute the LAT at that scan line.

Shadow Search Features

Figure 9:
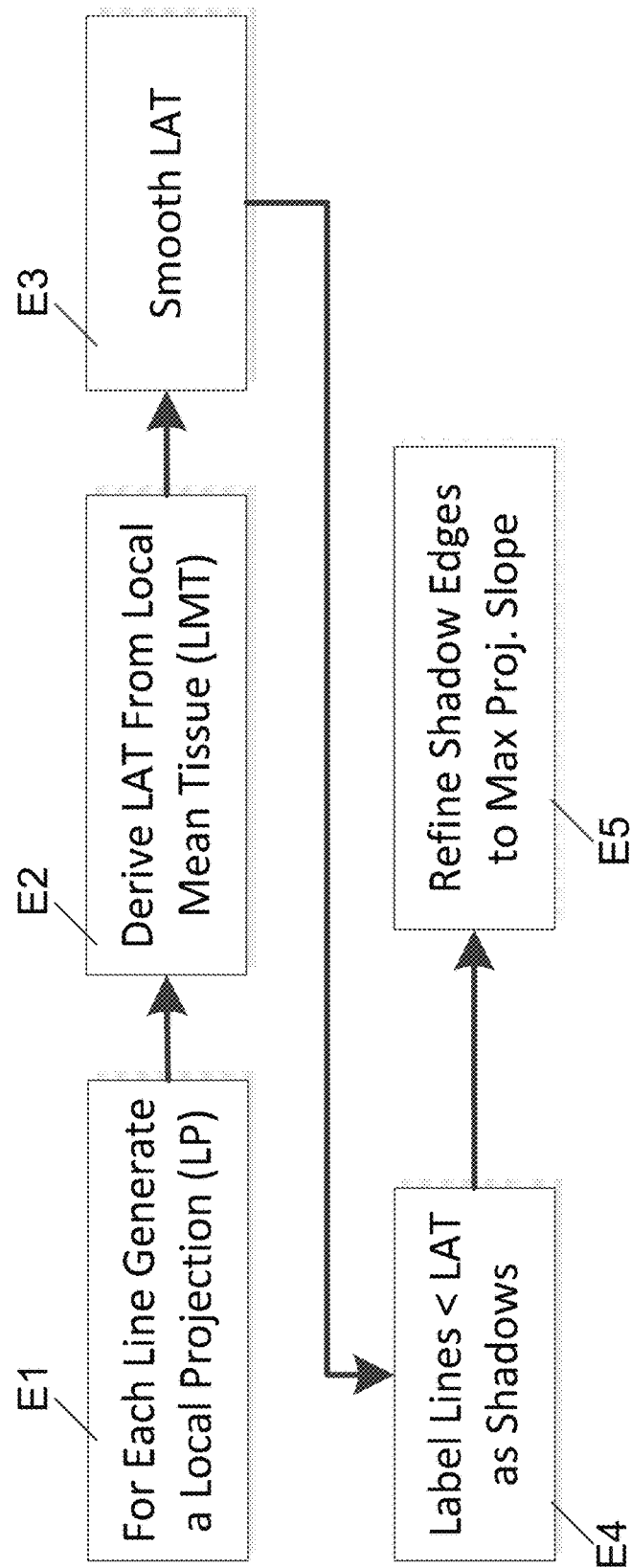
FIG. 9 is a process flow chart that illustrates an exemplary shadow search method according to an illustrative embodiment of the disclosure.

The shadow search method uses a locally adaptive threshold over the line projections to determine shadow regions. The determination of the locally adaptive threshold is the key component of the shadow search method. The method computes a locally adaptive threshold for each line as shown in FIG. 8. The diagram in FIG. 9 illustrates the shadow search method steps. The shadow search method can be implemented using various algorithms that include one or more steps to transform or otherwise operate upon and identify shadows generated by one or more intravascularly measured objects.

The shadow search method computes a projection intensity value range. This is an overall range in one embodiment. The next step calculates the mean of the tissue as the mean of all values where the projection is greater than the middle of the projection intensity value range. The mean of the tissue (MT) is used in the next steps.

Still referring to FIG. 9, for each scan line L, a local projection (LP) is created Step E1. The list of local projection values is sorted and capped at MT. The local mean tissue (LMT) value is derived or computed as the mean of the local projection values in the top half of its range Step E2. The locally adaptive threshold for line L is computed as half the LMT in a windowed neighborhood about line L. Finally, the locally adaptive threshold is smoothed with a moving average filter or other smoothing process Step E3.

The scan lines are searched and if the projection falls below the smoothed locally adaptive threshold for that line, the line is marked as belonging to a shadow Step E4. The method defines a new shadow if the previous line is a non-shadow line. The method also checks for the special case of shadow wrapping around the edge of the image. Due to the nature of the polar coordinate system, scanline 0 is directly adjacent to the last scanline, and so in the wrapping case, the shadows on the edges of the image are merged.

Shadow Refinement

In one embodiment, the shadow search includes the step of refining the shadow start and stop locations to the location of maximum slope on the projection Step E5. The locations are not adjusted in the case of shadows that consist of a single scan line only.

Validated shadows are further distinguished by comparing each shadow to all other shadows on the frame. Shadows that overlap are merged into a single shadow, and the duplicate shadow is removed. The method accounts for cases where shadows wrap around the image.

The shadow detection methods operate upon various inputs. In one embodiment, the inputs to the method are pointer to the frame image buffer, near offset values and far offset values computed as described herein. Shadow detection methods contain several sub-steps. These sub-steps, which can also be methods steps in their own right include: computing line projections; generating local adaptive threshold; performing shadow labeling; refining shadow edge positions; and performing shadow refinement. These steps are common to shadow detection within the guidewire detection and stent detection algorithms.

Examples and Results of Shadow Detection Excluding Bloom Brightness

Figures 10A, 10B:
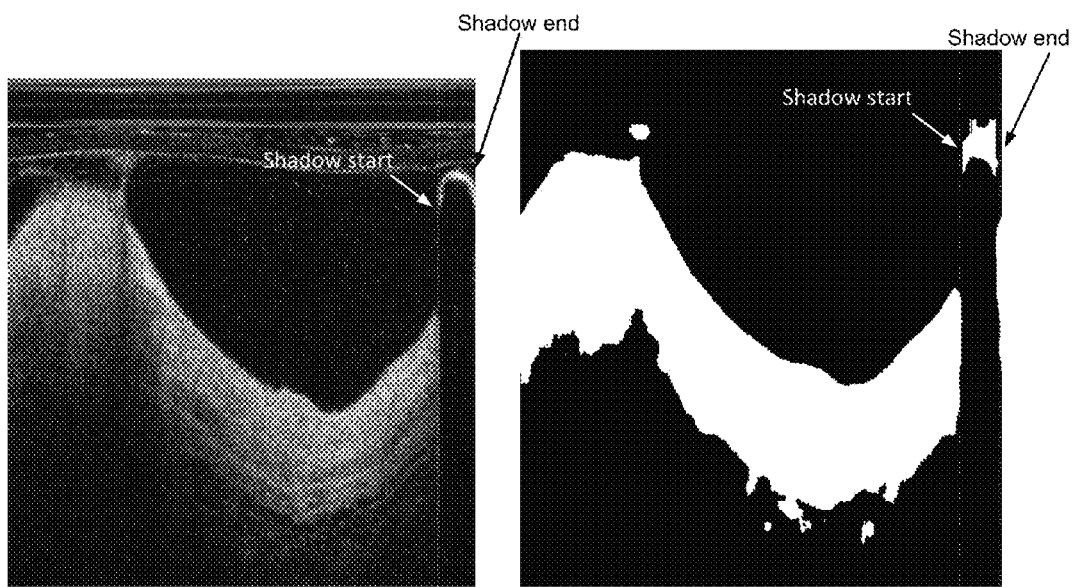
FIG. 10A-D are intravascular images (FIGS. 10A and 10B) and binary masks thereof, respectively (FIGS. 10C and 10D) illustrating the detection of a shadow region according to an illustrative embodiment of the disclosure.
Figures 10C, 10D:
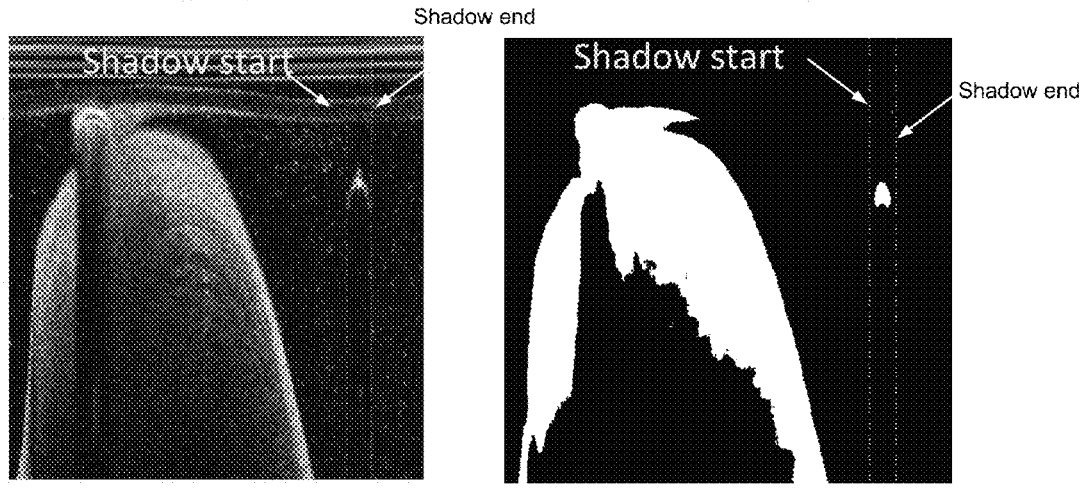
Figure 14A:
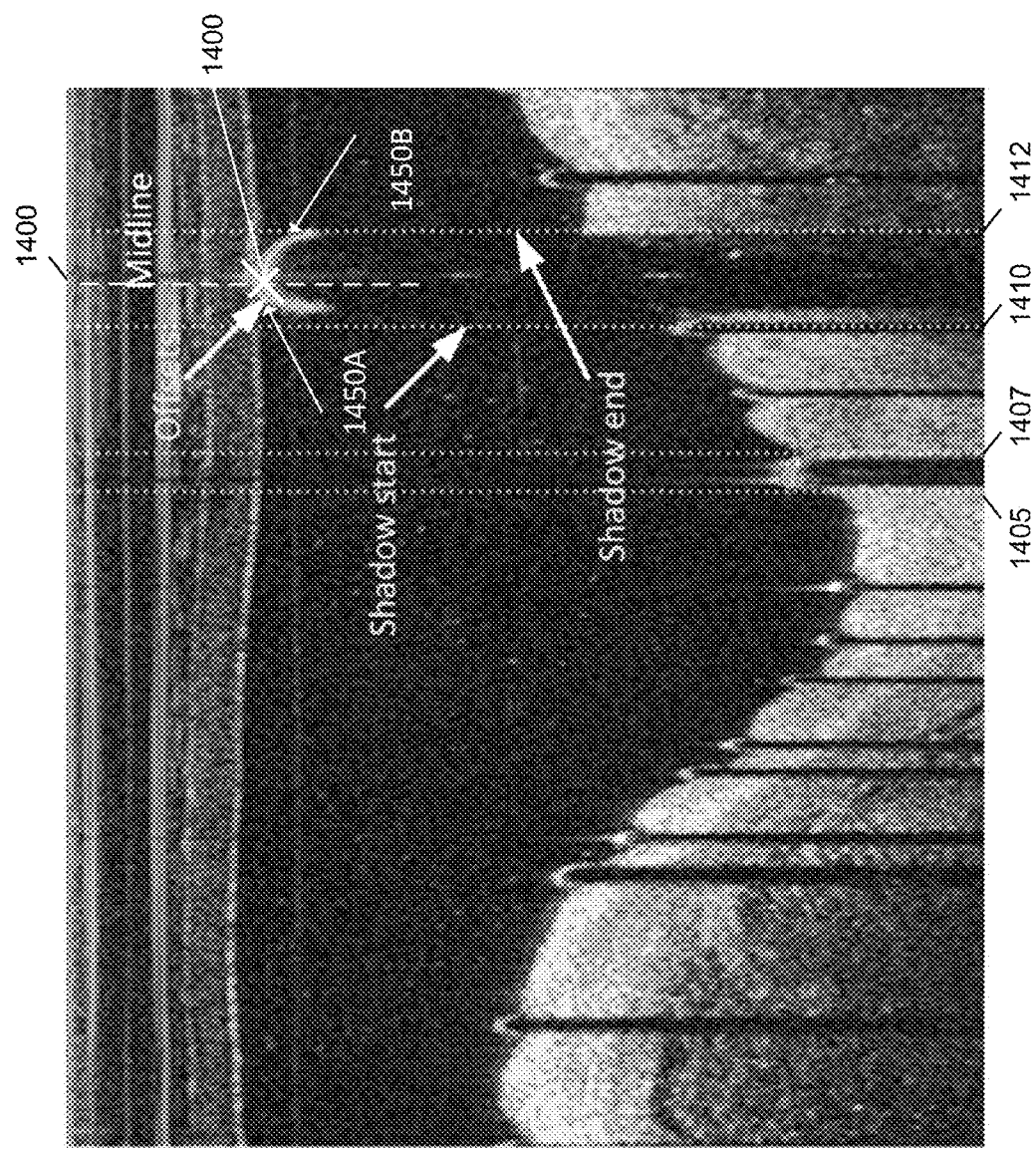
FIG. 14A is an intravascular image after the application of one or more intravascular data detection modules showing guidewire position according to an illustrative embodiment of the disclosure.
Figure 14B:
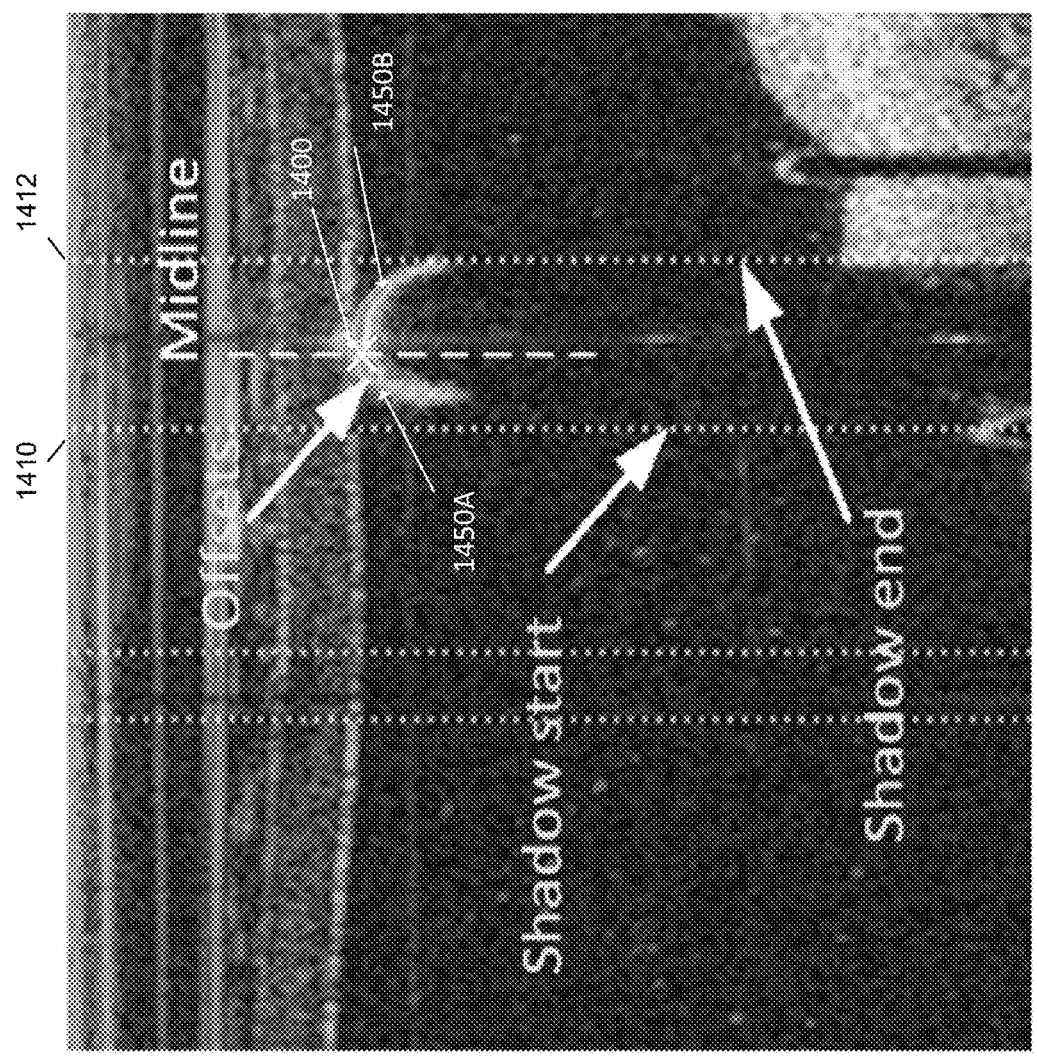
FIG. 14B is a magnified view of a portion of FIG. 14A according to an illustrative embodiment of the disclosure.

The images shown in FIGS. 10A-10D shows the position of the detected shadows in two OCT images. FIGS. 10A and 10B show two OCT images and the locations of shadows starting and ending. FIGS. 10C and 10D show the binary masks generated from FIGS. 10A and 10B, respectively. FIGS. 14A and 14B show further details relating to OCT images and the position of shadows relative to offset and midline values.

Detection of Guidewire Offsets in Shadow Regions

Figure 11:
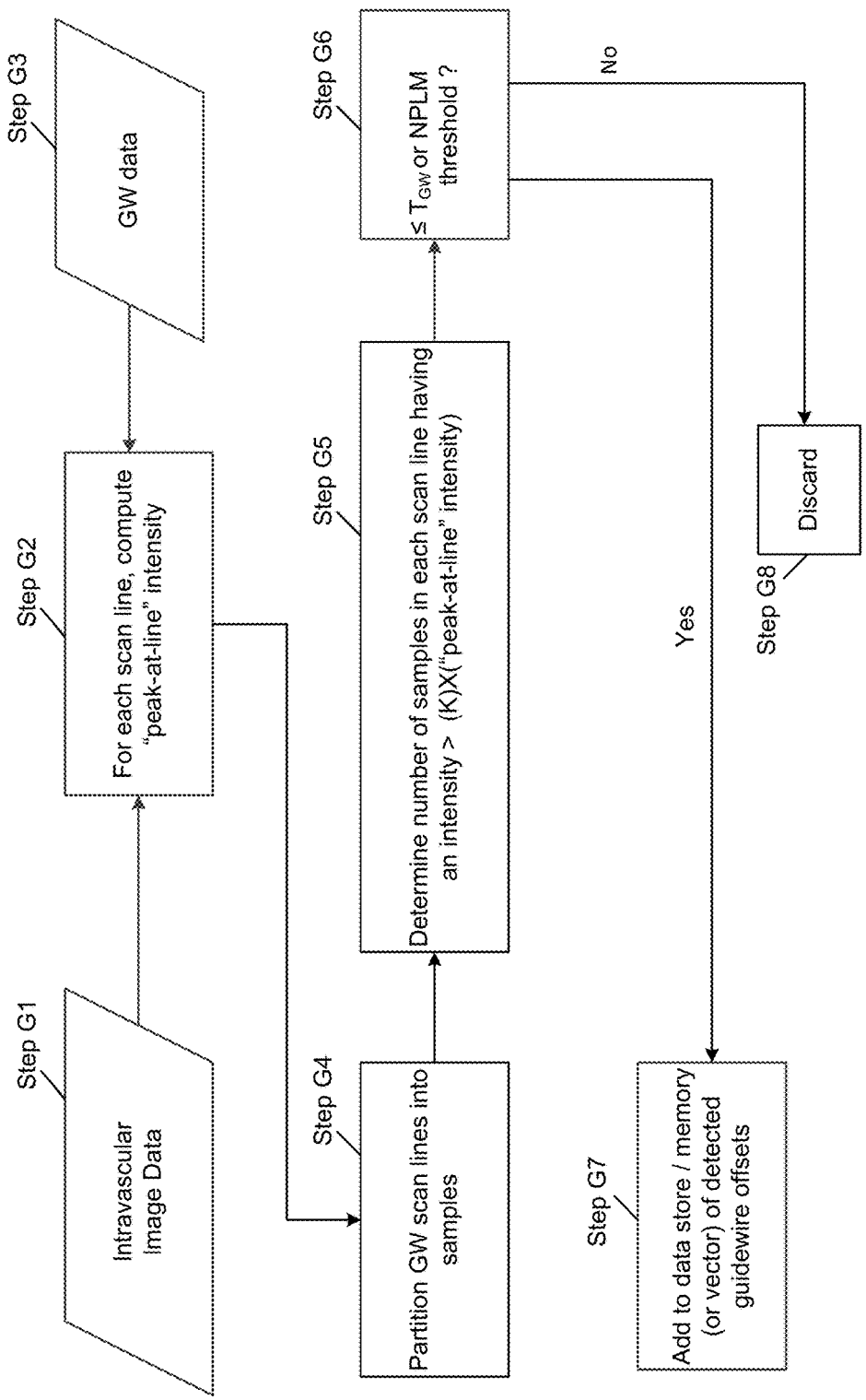
FIG. 11 is a process flow to determine guidewire offset positions from an intravascular dataset according to an illustrative embodiment of the disclosure.

After shadows have been identified and refined, the method detects the offsets for every scan line in a shadow region. In one embodiment, the guidewire offsets are computed for each scan line in the shadow region using a NPLM method. An exemplary implementation of this method is shown in FIG. 11. The methods described herein can be used with metal objects such as guidewires that can be detected in an intravascular image. Blood vessel tissues, lipid plaques, and other intravascular features also reflect coherent light, making it difficult to distinguish guidewire in OCT images based on reflectivity alone. Further, as noted above, shadows cast by guidewires are not detectable against the backdrop of a side branch lumen. To solve this problem, an algorithmic method referred to as Naïve Peak at Line Measurement (NPLM) is provided for detecting candidate guidewire shadows. Additional details relating to the NPLM method are described in co-pending U.S. patent application filed on Dec. 18, 2015 entitled "Detection of Stent Struts Relative to Side Branches" having Ser. No. 14/975,462, the content of which is incorporated by reference herein in its entirety.

The NPLM method to find the offset position for a scan line is shown in FIG. 11. The method can be used to operate upon intravascular image data (provided in Step G1) and/or GW data (provided in Step G3). For each scan line within the detected shadow region, the peak intensity is computed Step G2, followed by the number of samples with intensity greater than $1/10^{th}$ of peak at line intensity. If this number is less than an empirically determined threshold, $T_{GW}$ the position of the maximum is marked as guidewire offset on that scan line Step G6. In one embodiment, the method includes the step of filtering or removing outlier offset values. In one embodiment, $T_{GW}$ is the NPLM threshold.

Figure 13:
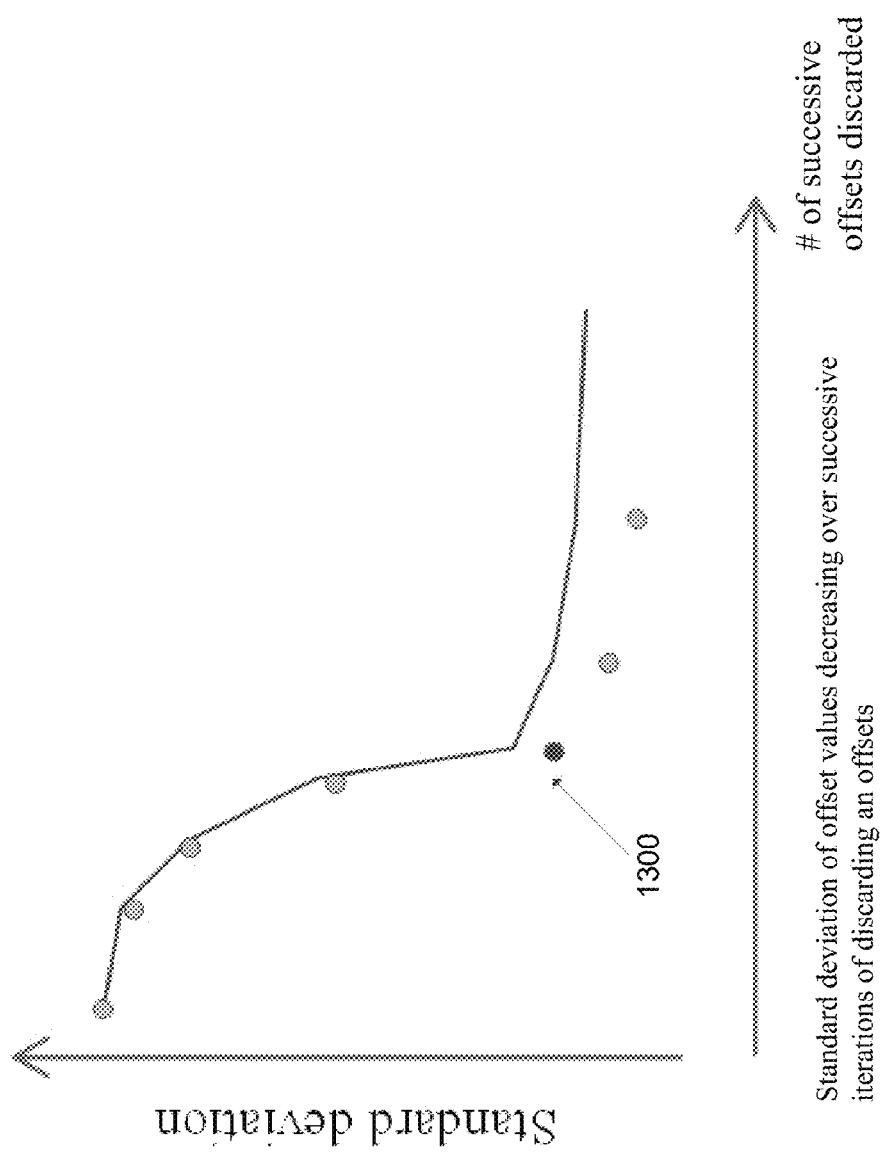
FIG. 13 is a plot of iterative standard deviations as computed by a method, such as implemented using a software algorithm, used to remove outliers of guidewire offset values for the purposes of identifying guidewire offset within a shadow, according to an illustrative embodiment of the disclosure.

The method removes the offset location farthest from the center, until it reaches the elbow point 1300 of sigma curve as plotted in FIG. 13, for the purposes of identifying the best fit or accurate guidewire offset within a shadow. If the product of peak-at-line and K is not less than the guidewire threshold $T_{GW}$, the scan line is discarded Step G8. If the product of peak-at-line and K is less than the guidewire threshold $T_{GW}$, then the scan line data is added to data store/memory of detected guidewire offsets Step G7.

In one embodiment, the method includes the step of determine number of samples in each scan line having an intensity>(K)("peak-at-line" intensity) Step G5. The value K is a proportionality or scaling factor such as the $1/10^{th}$ value described above when referencing $1/10^{th}$ of peak at line intensity of peak at line intensity. In one embodiment, K ranges from greater than about 0 to less than about 0.5.

In one embodiment, the guidewire detection method includes checking for offset validity. Re-compute the offset location if the offset location is consistent with detection within the catheter sheath. More specifically, offsets are recomputed if they fall within a fraction of the fiducial diameter, or if they fall within the detected sheath when using a catheter that has the doped sheath.

Guidewire Offset Detection with Peak Exclusion

Figure 12:
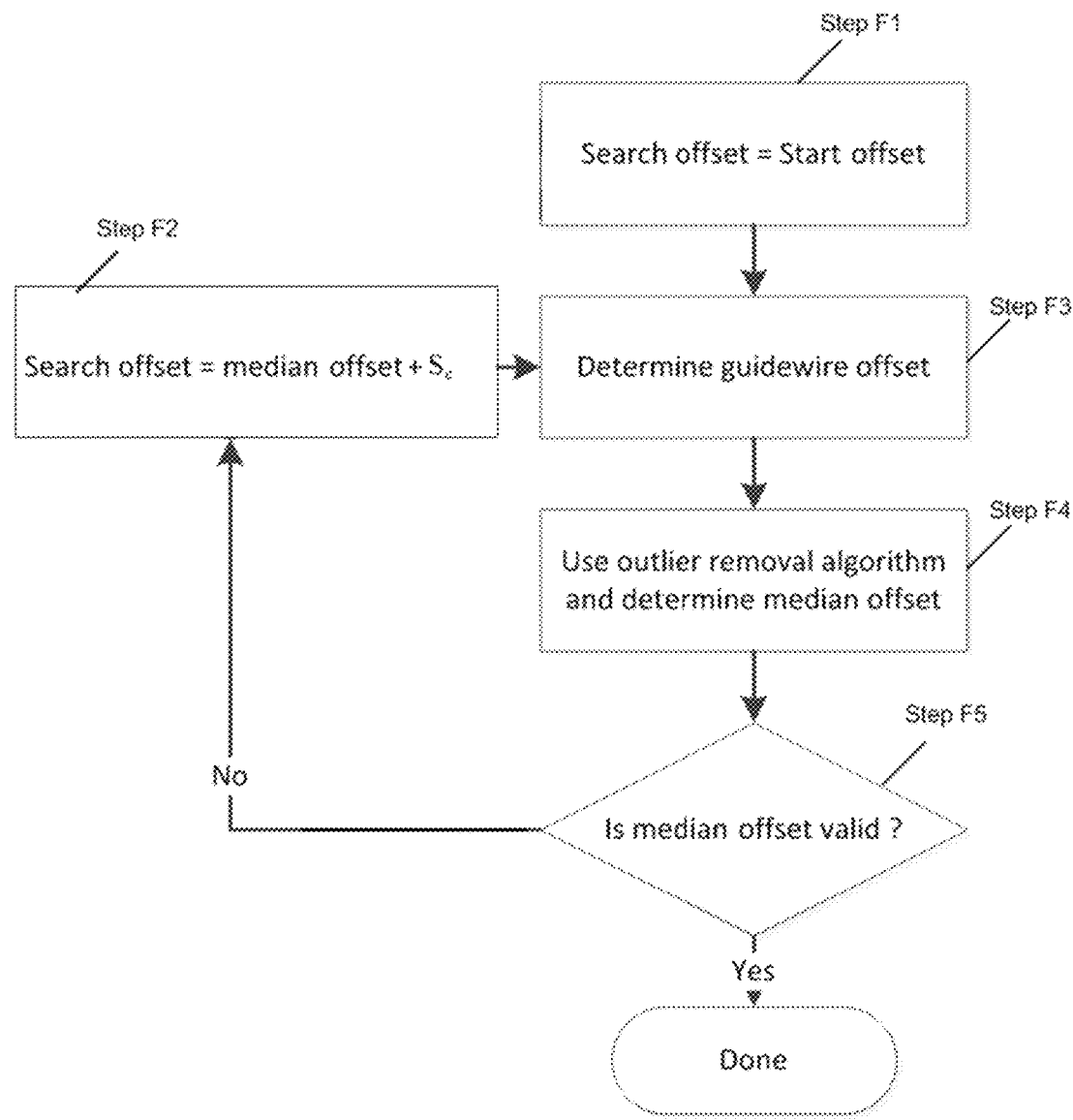
FIG. 12 is a process flow chart of various guidewire detection and related intravascular data processing steps to avoid erroneous signal detection within a delivery catheter according to an illustrative embodiment of the disclosure.

An exemplary method to find a guidewire offset while excluding peaks associated with structures disposed within the delivery catheter is shown in FIG. 12. This particular process flow in FIG. 12 relates to an exemplary embodiment in which the objective is to not detect signals such as peaks within the imaging catheter/intravascular data collection probe as the guidewire. For example, reflections or other spurious signals can be bright and appear as a guidewire. The process of FIG. 12 uses the inputs from FIG. 11 (Step F1) and includes steps to deal with certain types of spurious signals. In some embodiments, this process can be used in the event that an imaging catheter/intravascular probe is in use that does not contain a doped sheath or other calibration component such that a priori information of the exact location of the catheter sheath is not available.

In some embodiments, a calibration feature provides such a priori information and the location of the catheter sheath that surrounds the optical fiber as part of the data collection probe is known. The median offset is considered valid if it is outside the fiducial circle Step F5. If it is inside the fiducial circle, the projection values are computed at median offset (window size of 200 microns) for regions inside and outside the shadow region. If the projection values are different, median offset is considered valid.

As shown in FIG. 12, in one embodiment, the guidewire detection method includes computing the median of the filtered offset locations to determine guidewire offset position Step F3. The method of FIG. 12 uses the information obtained using the method of FIG. 11 relating to the guidewire offsets obtained. Initially, offsets are searched to find the start offset Step F1. The median of the filtered offset locations in the shadow region is used as the offset position of the guidewire in one embodiment. The offset position indicates the distance of the guide-wire edge from the center of the imaging catheter. The outlier rejection method is based on iteratively removing the farthest point from center and computing the standard deviation Step F4. If the median offset is not valid the median offset is expanded outward by a scaling factor $S_C$. The search is then performed with respect to the median offset expanded by the scaling factor $S_C$ Step F2.

If the imaging probe is receiving a spurious signal from a reflective surface to create a bright ring in front of the guidewire, the process of incrementing the offset with $S_C$ can push the offset past the ring to allow an actual guidewire to be found. The process of FIG. 12 is repeated until the slope of standard deviation plot decreases (see FIG. 13). FIG. 13 shows a plot of standard deviations relative to the number of successive offsets discarded. Thus, in one embodiment, a set of the offsets is generated. Point 1300 indicates the elbow or turning point of the curve.

The methods for finding the offset location can include the NPLM method and others. The offset position of the guide-wire for each scan-line inside the shadow region is saved in memory. The outliers are removed. After the outliers are removed, the median is computed to determine guidewire location. The position of the guide-wire and the corresponding start and stop scan-lines of the shadow region is saved in one or more electronic storage devices with a suitable identifier such as for example scan line and position identifiers. In one embodiment, the method includes determine offset location using NPLM method, remove outliers, and computation of median offset of the guidewire.

FIGS. 14A and 14B show an example of detected guide-wire on the image. The green dots shown on the curve bordered by endpoints 1450A and 1350B show the offset position for the scan lines between the start and stop of the shadow region. The 'Midline' position is computed by taking the average of the start 1410 and stop 1412 of the shadow region. The 'Average offset' is computed by taking the median of the offset positions after outlier removal. In each figure, the white cross 1400 shows the detected position of the guidewire.

Carpet View Generation

Carpet views are used in the multi-frame processing stage to determine valid segments based on whether they overlap shadow regions. FIGS. 15A-15G and 17 show various details relating to carpet view images and detection and image processing steps applied thereto. The projection values in the lumen region are used to generate the carpet view. In one embodiment, carpet view generation is performed during single frame processing. The lumen region is defined by the near offsets and thickness. Each frame generates a single line in the carpet view images. Therefore, the size of the carpet view will be (Number of lines per frame×Number of frames).

FIG. 15A is an exemplary carpet view image 1440 showing stent strut shadows 1450, guidewire shadows 1455, 1460 and shadows from the mesh of a delivery catheter 1470. The frames are arbitrarily labeled 0 through frame N. The scan lines are likewise labeled scan lines 0 to scan line N. If rolled into a tube, Scan line 0 would be adjacent to Scan line N. On the right side, two guidewires are shown 1455 and 1460. Given the unrolled nature of the image 1450, part of guidewire 1460 is also shown on the bottom left side. FIG. 15A is an image shown before the performance of a binarization step. The middle band 1454 shown is the tip of the guide catheter 1470. The guide catheter 1470 is in the bottom half of the image. The elongate and snaking but continuous paths of guidewires 1455 and 1460 are clearly visible in this image and thus a basis to perform GW detection and to validate candidate GW detection.

Figure 15B:
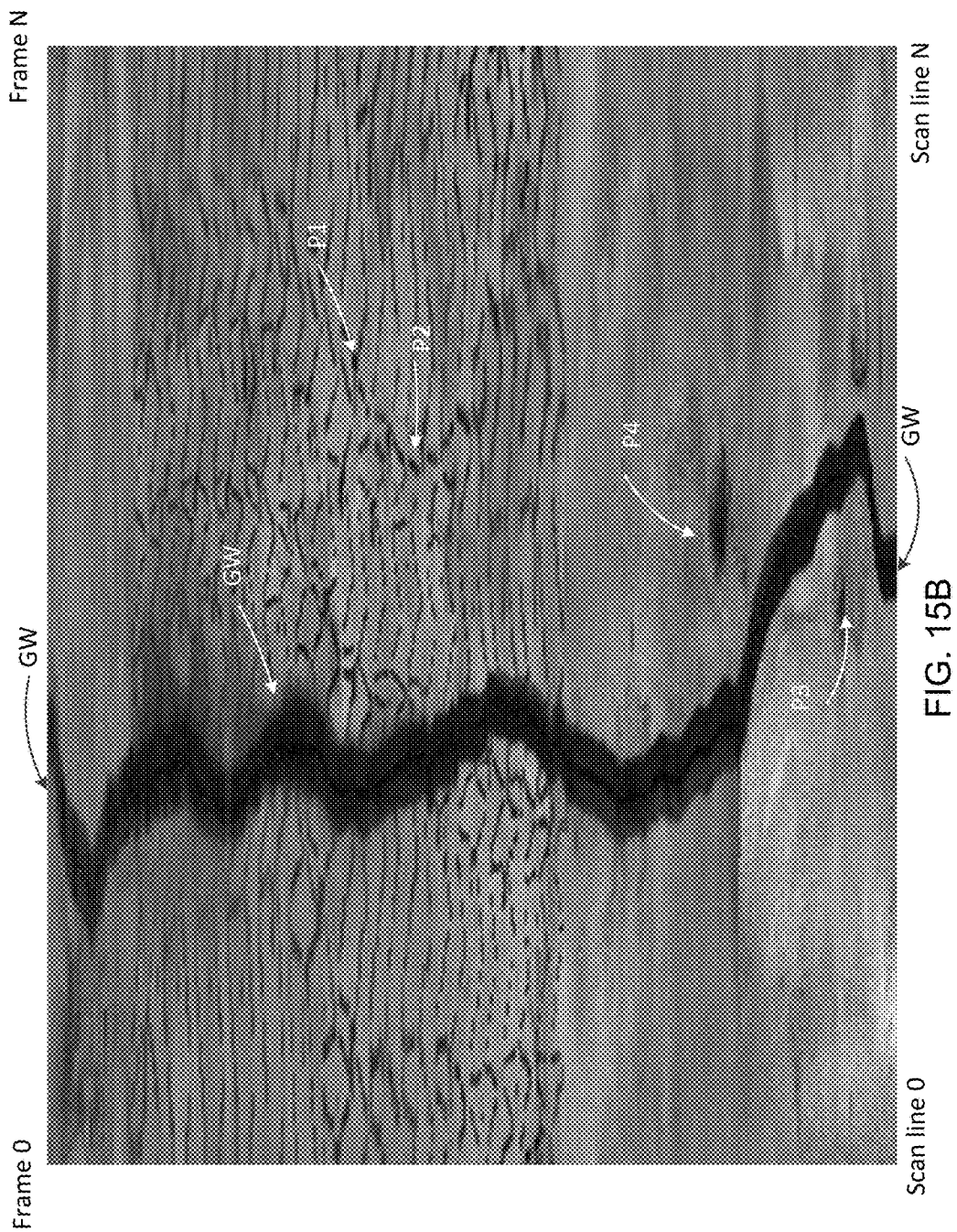
FIG. 15B is an exemplary raw carpet view image showing guidewire shadows and various other shadows according to an illustrative embodiment of the disclosure.
Figure 15C:
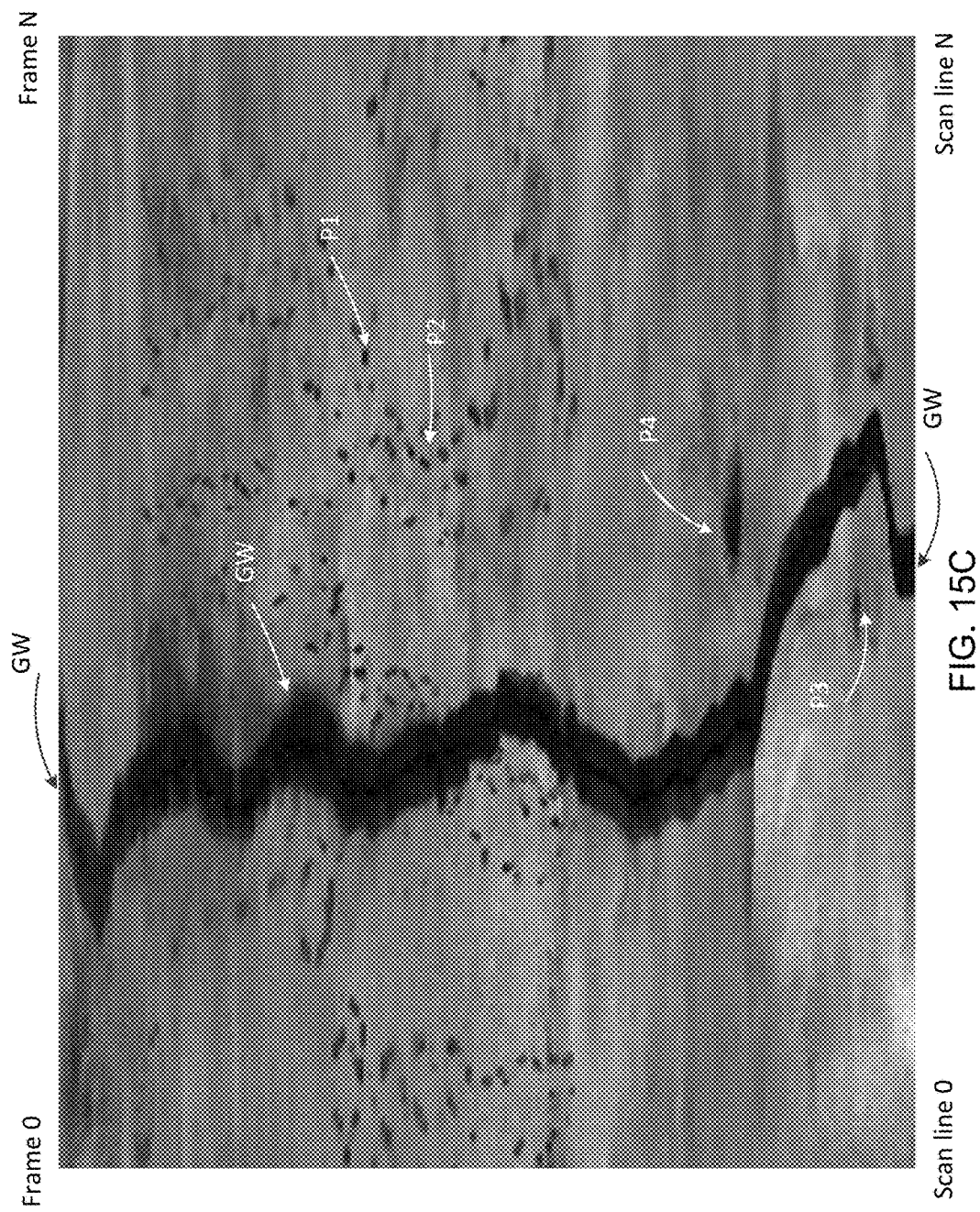
Figure 15F:
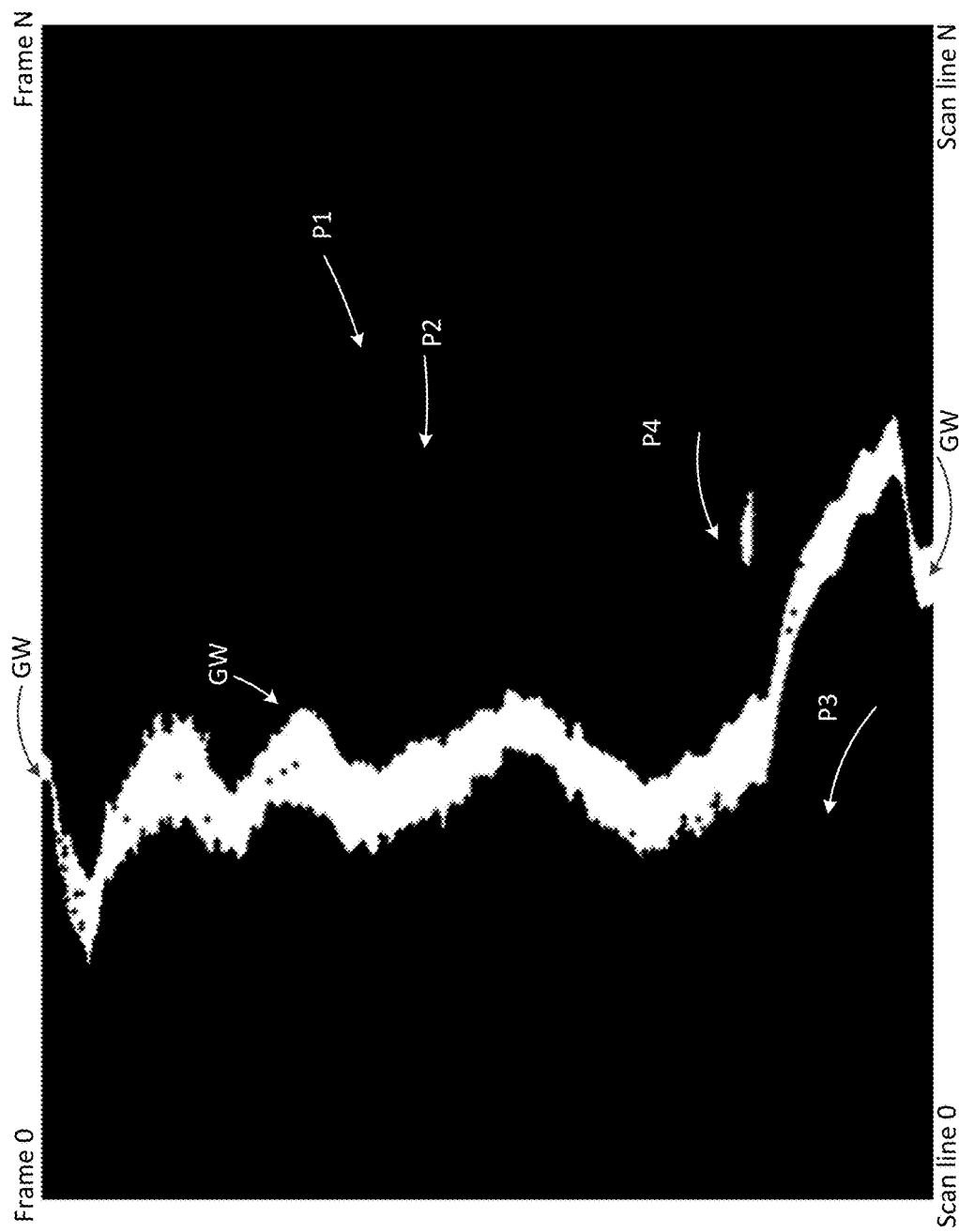

FIG. 15B is an exemplary raw carpet view image showing guidewire shadows and various other shadows according to an illustrative embodiment of the disclosure. FIG. 15B is a grayscale carpet view prior to the application of a series of image data processing steps. In FIG. 15B and FIGS. 15C-15G, a guidewire GW is shown. A cluster of stent struts are shown at points P1, P2, P3 and P4 show other shadows that are not related to the GW. These various points P1, P2, P3 and P4 are references that are in the same position for FIGS. 15C-15G. The frames of the figures are also labeled from 0 to N, wherein N is the total number of frames of data collected during an intravascular pullback using a data collection probe. In one embodiment, P4 can include a side branch.

Figure 15G:
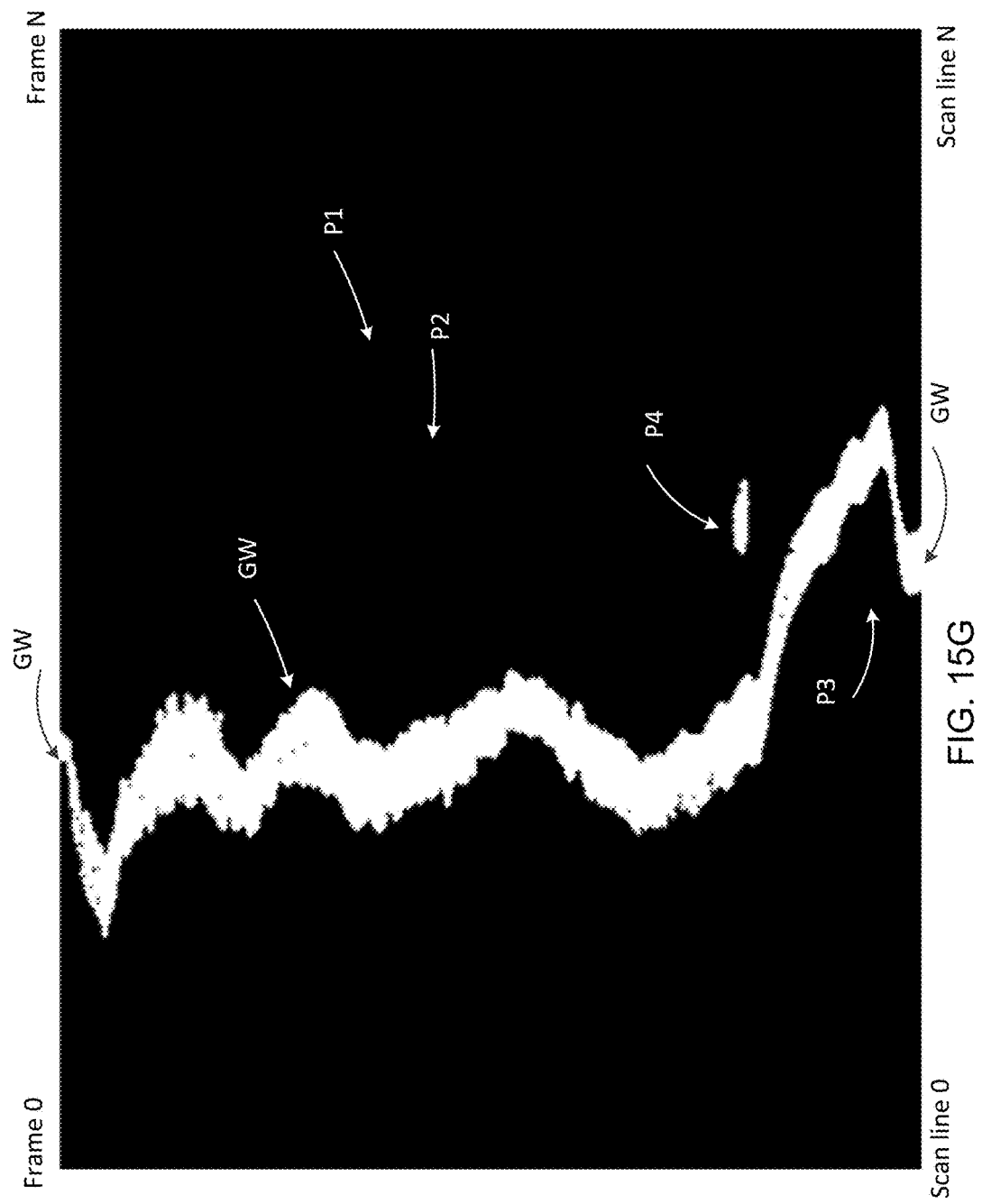

FIGS. 15C-15G are exemplary images after the application of various image processing steps on the carpet of view of FIG. 15B. These steps can include performing a morphological closing (FIG. 15C), performing a binarization process to create a binary carpet view mask (FIG. 15D), performing an erosion process (FIG. 15E), performing a small object removal process (FIG. 15F), performing a morphological closing (FIG. 15C), and performing a dilation process (FIG. 15G). In one embodiment, FIG. 15G represents the final carpet view mask suitable for use with the various GW detection steps described herein. The morphological closing process gets rid of most of the stent struts as can be seen by comparing the top half of FIGS. 15B and 15C. The binarization process quantizes the information in the grayscale image and as part of that process excludes the struts based on their intensity thresholds of the stent struts and any guide catheter shadows or other artifacts or reduces their intensity in the carpet view. The dilation and erosion steps further improve the carpet view such that the guide-wires are visible and not obscured by stents or other shadows.

Multi-Frame Processing: Defining of Guidewire

Prior to constructing a representation of the guidewire, certain guidewire features are first defined. The multi-frame processing method refines the guidewire points based on information derived from analyzing the detected guidewires across multiple frames. In one embodiment, steps of multi-frame processing of guidewire detection include one or more of the following create segments as connected frame detections; create guidewire model using connected segments; and post processing to disambiguate the wires and trip false positive detections at the end of the wire models. The input to this stage is vector of guidewire detections in each frame. The detections are processed from the proximal to distal end of the recording of frames of data from the intravascular pullback.

During segment creation stage, the detections in each frame are checked to see if they can be linked to any of the existing segments. If detection can be matched to only a single segment, the detection is added to the vector of detections associated to that segment. If detection can be matched to multiple segments, then it is considered a merge and a new segment is created (segment 3 in figure above). If two detections can be matched to single segment, then it is considered a split and each detection starts a new segment.

Figure 16:
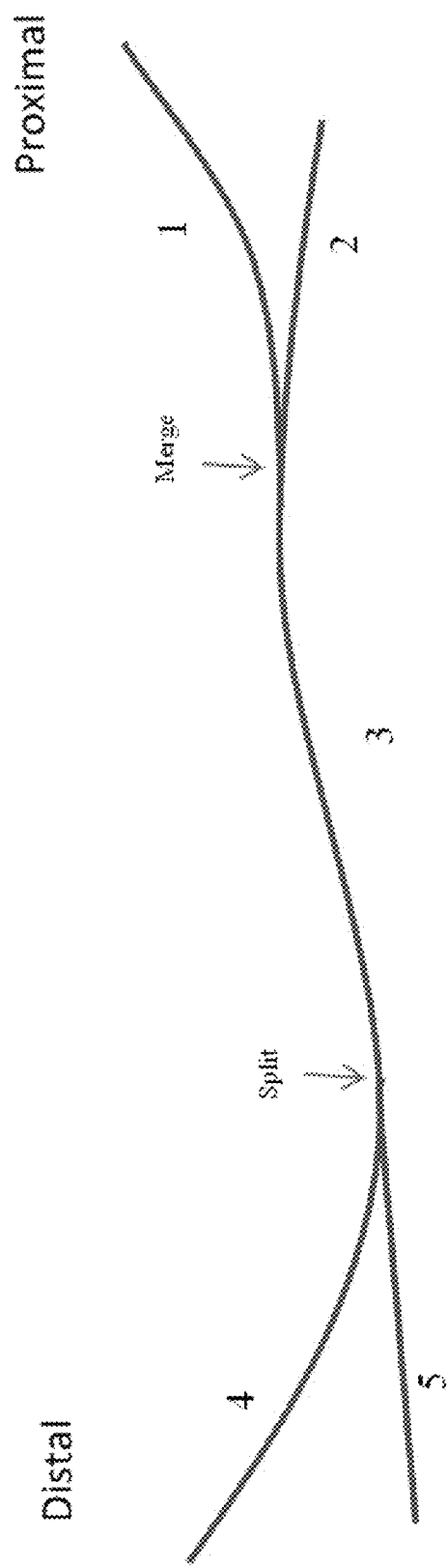
FIG. 16 is a schematic diagram of guidewire segments and splits and merges thereof suitable for segment definition and detection using methods according to an illustrative embodiment of the disclosure.

The connected model of the guidewire is then created by associating segments to the guidewire. For example, in FIG. 16, guidewire 1 is associated with segments (1, 3, and 4). Similarly, guidewire 2 is associated with segments (2, 3, and 5).

The multi-frame processing occurs in a multi-frame update component of the guide wire detection software module or other software module of the pipeline. In one embodiment, as shown in FIG. 4, one or more method steps are performed that include Processing of carpet view image to generate carpet view mask (Step A4)

Generating a set of guidewire segments (Step A5)

Removing spurious segments (Step A6)

Linking of detections to form segments and establishing parent/child relationship between segments (Step A7)

Linking of segments to create wires (Step A8)

Removing duplicate wires (Step A9)

Post processing (clean up/error reduction) (Step A10)

Additional details of these steps are described with regard to FIG. 4 and as otherwise described and depicted herewith. In one embodiment, one or more of the steps above are performed using a frame update function or operator. In this way, frames of image data can be updated to remove duplicates or otherwise modify or enhance a frame of data such that it includes validated information about a detected guidewire or guidewire segment. In one embodiment, the steps discussed above are performed using a single-frame processing implementation or a combination of single-frame and multi-frame processing.

Carpet View Mask Creation

The carpet view mask is computed and used as an important feature for removal of false positive segments and computation of scores for segments and wires. Segments which do not overlap the carpet view mask are invalidated. The carpet view mask image is created by processing the carpet view image. In one embodiment, the carpet view mask is a binarization of the carpet view image such that certain regions are dark or "off" while other regions are bright or "on." As shown in the various carpet view binary masks, the segments that form elongate guidewire segments correspond to the bright/white "on" regions. Thus, in one embodiment candidate guidewire segments are identified based on intersection of the candidate segments with "on" regions in the binary carpet view mask. In FIG. 17, for example, a carpet view mask 1700 is shown. In the mask 1700, a guidewire 1705 is formed from multiple segments that are part of the guidewire. The stent struts 1720 do not form the same connected pattern and zig zag without forming an elongate guidewire of "on" regions in the mask, even though individual struts are bright.

In one embodiment, a method for creating a carpet view mask image include performing grayscale dilation using disk shaped structuring element, performing grayscale erosion using a disk shaped structuring element, and computing the minimum and maximum of the carpet view image. With $I_{min}$ as the minimum grayscale value and $I_{max}$ as the maximum grayscale value of carpet view image, generate an image by scaling the carpet view by mapping $[I_{min} \ldots I_{max}]$ to $[0 \ldots 255]$. In one embodiment, the method generates a histogram of the generated 8-bit grayscale image. The histogram is used to discard the top and bottom 5% of all intensities. The low and high extrema of remaining intensities are denoted $t_l$ and $t_h$ respectively, and are used as upper and lower cutoff values in computation of the image threshold value as described in the next paragraph.

The method can include computing the lower and upper cutoff threshold based on a percentage of the total number of pixels (TNP) such as a TNP value of between greater than 0% and 20%. Threshold of carpet view image using threshold value of $t_l+(t_h-t_l)$TNP or another metric is generated. The method also performs binary morphological erosion (FIGS. 15C and 15E) to remove narrow regions using a disk shaped structuring element. Examples of these and other processes to clear/clean a binary carpet view mask are shown in FIG. 15B-15G. Small object detection and removing small blobs are performed. Small objects, such as blobs with area less than N pixels are removed from the image. N ranges from greater than 5 to 200 in one embodiment. The method also includes the step of binary morphological dilation using a disk shaped structuring element (See FIG. 15F). Using one or more of the foregoing steps, the carpet view is generated.

Segment Creation Through Linking Detections (Segment Linking)

Segment creation starts from the proximal end of the pullback. On startup, the method creates new segments from the detections in the first frame starting from the proximal end. In subsequent frames, the method checks if the detections can link to the existing segments. The distance between the tail of the segment and the detection is computed and if the distance is less than a certain threshold, the detection is considered for linking. The direct distance is computed as $$D=\sqrt{d_x^2+d_y^2+d_z^2},$$

where $(d_x,d_y,d_z)$ is the distance between the tail of the segment (last detection in the segment) and the detection under consideration. The compressed distance is computed as, $$D' = \sqrt{d_x^2 + d_y^2 + \left(\frac{d_z^2}{k^2}\right)},$$

where k is the compression factor. The value of compression factor is 10. If the value of D' is less than 300 microns, the detection is considered for linking to the segments depending on the linkage mode. During this process a vector of segment and detection linkages is created.

Additional Features Relating to Guidewire Segments and Geometric Characteristics As described herein, in one embodiment guidewire segment linking is performed based on proximity through the Euclidean distance measurement. An another embodiment, the guidewire detection process links segments through extrapolating existing segments into the frame containing each subsequent detection and determining which extrapolated segment lies closest to the detection. This extrapolation is performed on segments which have a minimum length of at least 0.6 mm. It uses the 3-D slope of the existing segment and extends the segment from its distal most detection in the direction of the 3-D slope. In order to link a segment to a detection, the extrapolated point from the segment typically lies within a narrow radius around the detection under consideration (example radius: 250 um). This method allows for more accurate linking of segments that have a high slope which has the potential to cause the distance metric alone to fail. In addition, in part, the methods include steps to handle three modes relating to specific characteristics of certain guidewire segments or wires are described below.

Mode 1: NEW ORPHAN SEGMENT: If detection cannot be linked to any segment, the detection starts a new orphan segment. If a segment can be linked to a single detection (one-to-one), then the new detection is added to the segment's list of detections. In this case, no new segment is created. If there is a gap between the back of the segment and the new detection, the gap is linearly interpolated by creating new detections.

Mode 2: MERGE: If multiple segments can be linked to single detection (many-to-one), then the new detection starts a new segment, and this is the case of a merge. If there is gap between the end of the parent segment and the new detection, the gap is linearly interpolated by creating new detections. The new detections are added to the end of the parent segment and then the parent is terminated. The new segment becomes child segment of the segments which can be linked to the detection (merge).

Mode 3: SPLIT: If multiple detections can be linked to single segment (one-to-many), each new detection starts a new segment. If there is gap between the back of the parent segment and the new detection, the gap is linearly interpolated by creating new detections. The new detections become part of the new segment. The new segments become the children of the segment which can be linked to the detection (split).

The systems and method of intravascular data processing can handle various types of complex connections. If multiple detections can be linked to multiple segments (many-to-many), an association matrix approach is used to link detections to the existing segments. If there are s segments and d detections, the size of the association matrix A is (d×s) matrix. The $(i,j)^{th}$ element of the association matrix corresponds to the distance between the $i^{th}$ detection and $j^{th}$ segment. An iterative approach to link detections to segments is used to link detections to segments. The detection-segment pair with the minimum value in the association matrix is determined.

In one embodiment, if the minimum value is less than threshold, the detection is linked to the segment. Once a detection/segment pair is linked, those elements are removed from consideration for linkage with other segments and detections. The remaining detections are matched to the closest segment. Similarly, the remaining segments are matched to the closest detection.

In one embodiment, guidewire segments are created during multi-frame processing. The function processes the detections from proximal to distal for each frame. The association of the segments and the detections are initially determined in this function, and software-based modules can include various functions and operators which processes the new detections to either extend the existing segments or create new segments (in case of a merge or split).

Segment Metric Computation Features

The segment creation process described in the previous section might create a number of extraneous segments which should be removed before the linking the segments to create wires. It requires computing metrics for each segment so that the segments with the lowest score are removed. This section describes the different metrics computed for each segment.

The metrics computed for each segment can include one or more of the following:

Fraction interpolated—Fraction of interpolated detections in the segment

Median width—Median width for all detections in the segment

Average slope—Computes the average of slopes using constituent detections. This particular slope feature is a measurement of the change of radial offset per change in longitudinal pullback length (dR/dz).

Fraction valid in carpet view—Checks the fraction of the frames in which the shadow region of the detection overlaps the carpet view mask.

Then the score of the individual segments is computed as (Length*(1−Fraction interpolated)*(Fraction valid in carpet view)). Then the scores of the ancestors are computed recursively and the maximum parent score is saved. Similarly, the scores of all the descendants of the segment are computed and the maximum child score is saved. The parent and child score includes segments self-score.

Then the weighted averages of segment width and segment slope for all the segments are computed. The weight factor is the score of the segment. Also, the deviation of the segment width from weighted average of segment widths is computed for all segments.

Spurious Segment Removal/Exemplary Validation Conditions

Figure 18:
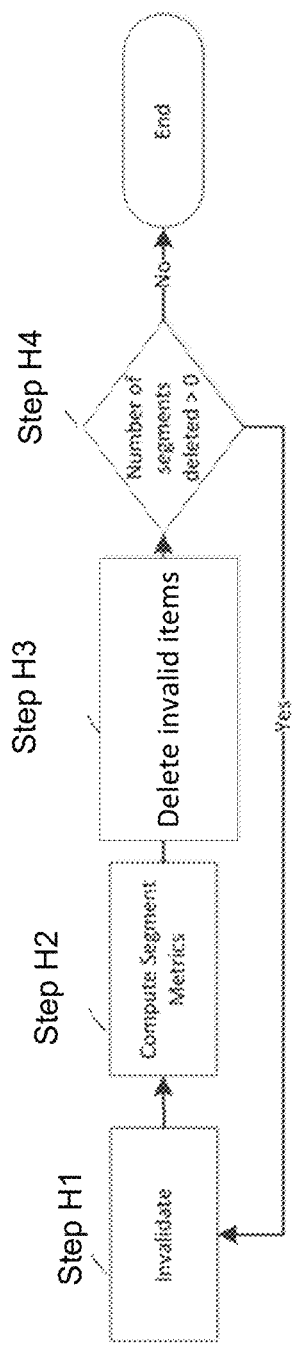
FIG. 18 is a process flow to remove spurious segments of guidewires according to an illustrative embodiment of the disclosure.

The metrics computed in the previous section are used to invalidate and remove spurious segments. This is an iterative process and the main steps are shown in FIG. 18. In one embodiment, the process of validation includes evaluating a family or group of connected segments and determining if the segments are invalid based on their score or geometric relationship to one or more segments in the group or other segments outside the group. For invalidation, the method iterates over the all the segments and computes a score and family-score of each segment. The method operates as a loop that invalidates segments that do not meet certain criteria. Thus, the initial step is to invalidate segments Step H1 based on one or more conditions or other factors being satisfied.

After invalidation, the system computes segment metrics Step H2. Once the metrics have been computed based on the various validation conditions, the method deletes segments that do not meet one or more of the conditions Step H3. In Step H4, if the number of segments deleted is not greater than zero, i.e., no deletions then the method stops. This follows because if all of the segments meet the various conditions than no segments would be deleted. If segments are deleted, the loop repeats. This follows because the deletions of some segments can change how other segments are viewed by the system. In one embodiment, spurious segments are identified for removal or filter from the valid segments using a set of exclusion rules to remove segments that have probability of less than about P of corresponding to an actual guidewire segment. In one embodiment, P is about 0.5. In one embodiment, P is greater than 0 and less than about 0.6.

In one embodiment, the method implements constraints or rules for validating and/or scoring segments using the methods described herein including the method of FIG. 18. In one embodiment, if the segment is short, such that the length of the segment is less than distance threshold and is not connected to anything other segments, the segment can be deemed invalid or the score of the segment is reduced.

Additional Exemplary Validation Conditions

In one embodiment, if a segment is doubly connected, but does not exceed a medium length threshold, the segment is rejected as invalid. In one embodiment, if a segment is singly connected, parent/child does not have a higher score, and has low segment score, the segment is rejected as invalid. In one embodiment, if a segment is more than X % interpolated it is rejected. In one embodiment, X is greater than 20 percent.

In one embodiment, if a segment is not predominantly on in the carpet view the segment is rejected as invalid. In one embodiment, if a segment is an orphan or barren and has width lower than a mean width it is rejected. In one embodiment, the deviation from the mean width ranges from about 10% to about 50%. In one embodiment, if a segment is in the guide catheter and has a slope greater than Y (or not in guide catheter and has a higher slope), the segment is rejected as invalid. In one embodiment, Y is greater than an average slope of a plurality of segments multiplied by factor that ranges from about 4 to about 10. In one embodiment, the plurality of segments is all of the segments being evaluated. In one embodiment, the slope is evaluated as the change in radius in a direction from an imaging probe verses a change in the longitudinal direction. Thus, the slope can be a measure of how much a guidewire is curving away from an imaging probe. A higher slope can correspond to a larger angle between wire a guidewire and an imaging probe/catheter.

Wire Linking Related Features

The segments created in the previous section are connected together to form wires. Exemplary methods to create wires from segments are described in more detail below. The basis by which frames are analyzed and processed as part of wire linking can vary in different embodiments. For example, in one embodiment frames are process in an order based upon the sequential arrangement of frames obtained during a pullback such as from proximal to distal or from distal to proximal. In one embodiment, frames are processed based on a starting point within or adjacent a guide/delivery catheter. In addition, in another embodiment, frames can be analyzed by processing frames in first direction and a second direction, the second direction opposite the first by starting at a point between the first and last frame of the pullback.

For example, a midpoint or center frame of the pullback can be selected to start the bi-directional scan/processing of the frames. In one embodiment, frames are analyzed based on groupings of frames that have been identified as validated or candidate guidewire segments. The sets of frames will typically correspond to sections of the guidewire. In one embodiment, the sets of frames are ordered based on which sets contains the most frames. That is, the set of frames which corresponds to the largest validated/candidate guidewire segment is processed first and then each next largest set is then subsequently analyzed and processed until all of the frames have been processed/analyzed.

Figure 21:
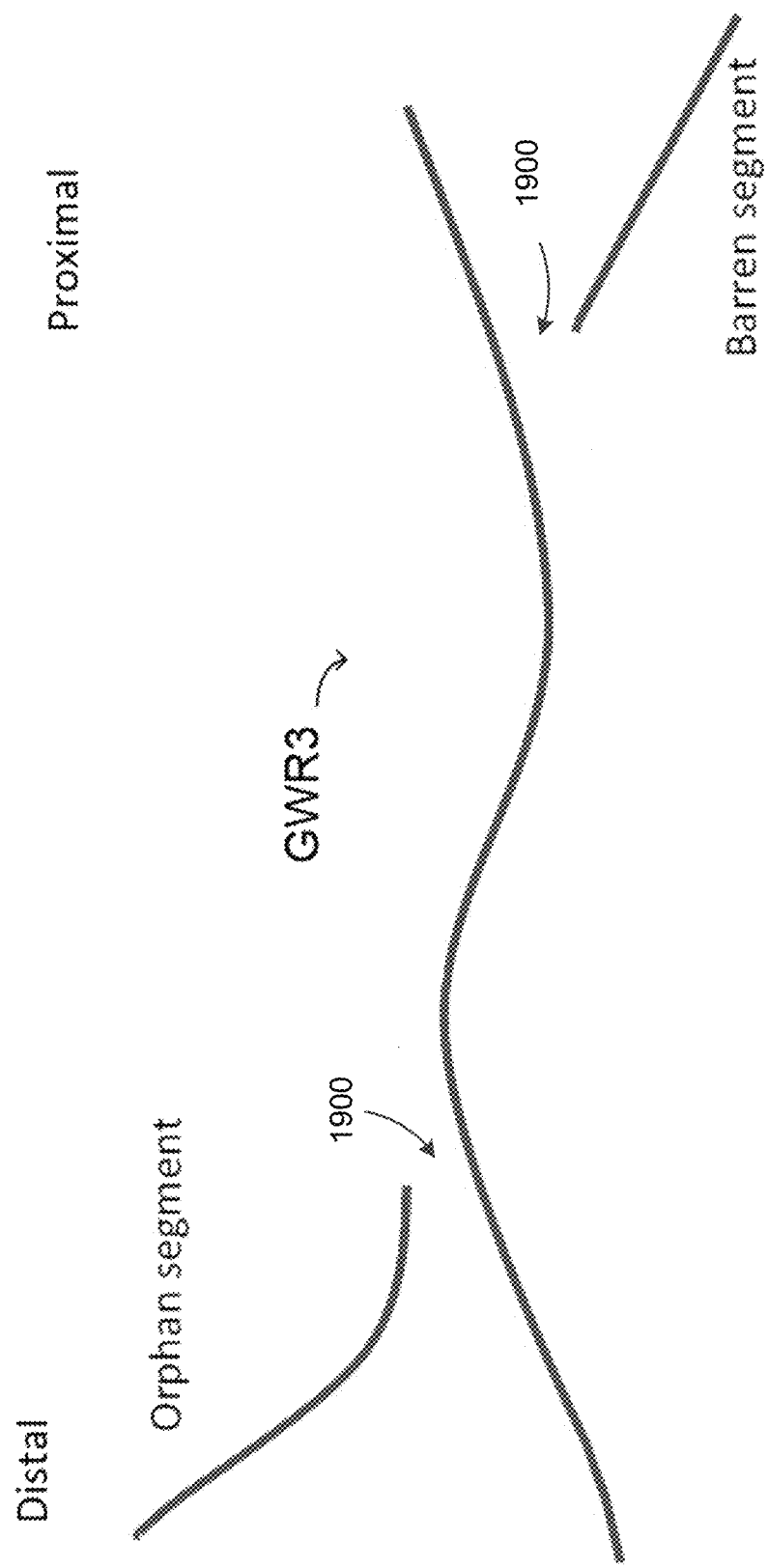
FIG. 21 is a schematic diagram of guidewire segments showing linking of barren and orphan according to an illustrative embodiment of the disclosure.

In one embodiment, the frames are processed from proximal to distal while scanning for detections and associating them to wires. For example, as shown in FIGS. 19-21, the frames are processed from proximal to distal (or right to left) as shown in these figures. Other sequences and methods to process the frames such as based on the longest contiguous segment being processed first can be used. Geometric connectedness from the carpet view mask can be used to identify such contiguous segments and map those to the underlying frames and further to the underlying guidewire shadow detections. In one embodiment, detections which are valid and have been associated with a segment are considered for inclusion in a guidewire representation. The linking of segments depends on the number of parent and child segments associated with the segment. The different cases are described below:

Case 1: Segment is Associated with a Detection that is Associated with a Wire

This is the simplest case. In this case, the detection is a continuation of a segment already associated with the wire. The detection is associated with the wires and the wires are associated with the detection.

Case 2: Segment is not Associated with a Wire

This implies start of a new segment. The detection is handled depending on the number of parent segments associated to its segment. The different cases are described below:

Case 3: No Parent Segment

The method first computes direct and compressed distance to the tail of each of the wires. The direct and compressed distances are described herein. The tail is defined as the last detection of the last segment of the wire. If the compressed distance to the closest wire is less than 500 microns, the new segment becomes the child of the last segment of the closest wire (distance measured using compressed distance) and any gap between the segments is interpolated by creating new detections.

In turn, the new detections become part of the parent segment. If the compressed distance to the closest wire is greater than 500 microns but the direct distance is less than 1000 microns, the new segment becomes the child of the last segment of the closest wire (distance measured using direct distance) and gap between the segments is interpolated by creating new detections. The new detections become part of the parent segment.

If no matching wire is found, the segment is checked to see if it is a candidate for new wire. If any of the following conditions are true, a new wire is started with the segment associated with the detection:

If the segment associated with the detection is inside the guide-catheter. In one embodiment, segment children score is greater than a certain threshold and fraction interpolated <0.2 and fraction valid in carpet view >0.75, a new wire is created and the detection, segment and new wire are associated with each other.

Number of parent segments greater than 1 is a case of merged guidewires in one embodiment. The method removes extraneous segment if the number of segments at merge is greater than the number of guidewire in the case when multiple guidewires are being used. Then the orphan segments are checked if they can be linked to the any of the parent segments in the merge. This would handle cases of occlusional loss due to a merge. If any segment is linked to the orphan segment, it is removed from the list of parent segments. The child segment is associated with all the wires associated with the parent segments. The detection is also associated with all the wires associated with the parent segments. The merge information containing information about the parent segment and the new detection is saved. The merge information is used when assigning the wires to the segments at a subsequent split.

Parent Associated with Multiple Wires

This is the case of a split in which the wires associated with the parent segment has to be split between the child segments. The method removes extraneous segment if the number of segments at split is greater than 2 (or N wherein N is the number of detectable separate guidewires in the imaging data).

In one embodiment, if any segment is linked to the childless segment, it is removed from the list of segments to be considered for split. The method looks for the previous merge involving the same set of wires and assigns the wires based on the merge/split mode. The merge modes can be colocation or occlusion. In colocation mode, the two wires merge by running side-by-side. In occlusion mode, one wire occludes the other. The colocation mode, the wires are assigned based on the order scanlines of the wires at merge and split. In occlusion mode, the wires are assigned based on order of offset of wires at merge and split.

Removing Extra Segments at Merge

During this step, if the number of parent segments is greater than 2, the segment with the smallest median width is removed from the list of segments considered for merge. If the narrowest segment has any children, the child-parent relationship is broken by removing the segment from the list of parents of the child segments, emptying the list of child segments of the narrow segment.

Removing Extra Segments at Split

During this step, if the number of sibling segments is greater than 2, the segment with the smallest median width is removed from the list of sibling segments considered for split. If the narrowest segment has any parent, the child-parent relationship is broken by removing the segment from the list of children of its parent segments and emptying the list of parent segments of the narrow segment.

In one embodiment, the method iterates through and operates upon elements of a vector or group of data and links detections to wires. In one embodiment, the software modules iterate through the detections in a frame. The guidewire detection software module associates wires, segments and detections. The software and associated method create a new wire and associates it with the segment and detection. In one embodiment, the method includes finding the closest tail of the wires and connects the segments if the distance is less than a separation distance threshold.

Occlusion Loss

In one embodiment, various methods can be implemented to handle the cases where connectivity of the segments is lost due to occlusion. In one embodiment, several exemplary types of cases are considered. The cases and various steps suitable to address them are described below.

Linking of Orphan and Barren Segments

Linking of segments at split with a barren segment. In FIGS. 19 and 20, the geometric guidewire representations GWR1 and GWR2, respectively, is indicative of what happens when guidewires cross one another yet the segment linking does not create the merge AND the split. The guidewire representation GWR1 is the case of "occlusional loss" in which the parent or child segment needs to somehow be associated with the split/merge. As noted herein, in one embodiment, the guidewire representations GW1, GW2, and GW3 are processed from a proximal position in the distal direction, which is from right to left in FIGS. 19-21. In addition, as shown, various breaks or separations 1900 are shown between different segments.

In FIG. 19, given that the frames (vertical/circular cross-sectional slices) are evaluated moving from proximal to distal, a segment that is detached from a parent segment when encountered on the proximal side is a barren segment in one embodiment. Also, in FIG. 19 the main guidewire representation GWR1 (or parent) splits into two guidewires on the distal side. Similarly, in FIG. 20, a segment that is encountered on the distal side after the main parent segment has been processed having a gap or break 1900 is an orphan segment. In FIG. 20, a merger is on the right side as two segments come together. A merge (on proximal side) is a split (on distal side) in an embodiment where segment processing moves from proximal to distal. In a split a guide wire segment/representation splits into two guidewire segments/representations.

In one embodiment, such a method first determines the segments associated with the child detections at the split. Then the vector of all the possible matching segments is determined. Then the segment closest to the last detection of the parent segment is selected. Based on the radial offset of the detections, the detection closest to the parent segment is matched. The remaining detection is consumed the wires associated with the parent segment Linking of segments at merge with an orphan segment is shown in the GW representation GW2 of FIG. 20. The method first finds all the orphan segments with the frame number less than the distal frame number of the parents at the merge. Then the segment closest to the child detection is found based on 3D Cartesian distance. The distance between the selected orphan and the parents (of merge) is computed based on radial distance. The orphan is matched to the parent closest to the orphan. If there is a gap between the closest parent and the orphan, the detections are interpolated and appended to the parent segment. The matched parent is removed from the list of parents.

Linking of Orphan and Barren Segments

As another example, segments are not linked earlier because of the large distance between segments. In this case, one wire essentially passes behind another wire as shown in the example of FIG. 21. This is handled by the case in which an orphan segment is connected to wire that is the best fit given the various conditions and constraints for linking.

Duplicate Wire Removal

Due to the presence of spurious segments, the method to link segments to create wires can create wires which are collocated along common segments. Sometimes these duplicate wires can have a score higher than the score of valid unique wires, resulting in valid wires getting discarded. This refers to the exclusion of all but the two wires having the highest wire scores. This step checks if the two wires are almost identical. If two duplicate wires are found, the wire with the lesser score is discarded.

Let $n_1$ denote the number of detections in first wire and let $n_2$ denote the number of detections in the second guidewire. The minimum detection count is computed as $$n_c = \min(n_1, n_2)$$

Using the segments associated with the wires, the total number of detections which are common to both wires is determined. Denoting the number of detections which are overlapping by $n_o$ the overlap ratio R is computed as $$R = \frac{n_o}{n_c}$$

If (R>0.95), the wires are considered as duplicate. This does handle cases when the segments are different but the distance between the segments is very small for a large number of segments. In these cases, the wires will be incorrectly identified as non-duplicate. To handle these cases, the method determines the longest run of detections in the wire where distance is greater than 550 microns. If the longest run-length is less than a run length threshold and (R>0.80), the wires are considered as duplicates. In one embodiment, the run length threshold ranges from about 200 to about 1000.

It is possible to have more wires detected by previous steps than exist in the imaging environment. As the algorithm supports establishing a cap or limit for the number of detected wires, this step selects the best N wires and invalidates the remaining wires. Thus, if N is set at 2 and 3 guidewires are detected, the two best candidate wires would be selected and the third wire would be excluded from further analysis and/or display. The wire score is used to select the wires. The score of a wire is sum of scores of the segments associated with the wire. Thus, a plurality of segments that define a given guidewire each contribute to its overall score which can be used as the basis for selecting the best candidate guidewires within the preset guidewire cap. The method selects the top N detected wires with the highest scores and rejects or otherwise invalidates the remaining wires.

Figure 22:
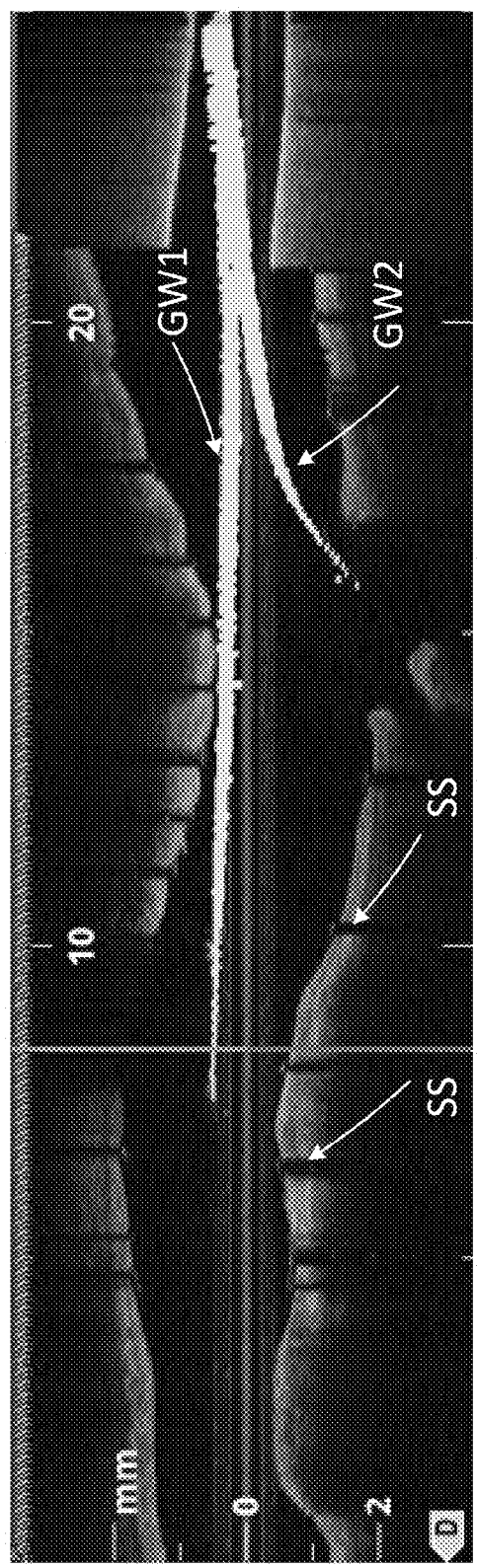
FIG. 22 is a cross-sectional or longitudinal display of an intravascular image with multiple guidewires shown as part of a user interface of a diagnostic system according to an illustrative embodiment of the disclosure.

FIG. 22 is a cross-sectional or longitudinal display of an intravascular image. The cross-sectional image includes two guidewires GW1 and GW2. The guidewires are as part of a user interface of a diagnostic system according to an illustrative embodiment of the disclosure. In one embodiment, the diagnostic system is an OCT system. The two guidewires GW1 and GW2 of FIG. 22 are also shown in FIG. 23A which provides a three-dimensional cut rendered view.

Figure 23A:
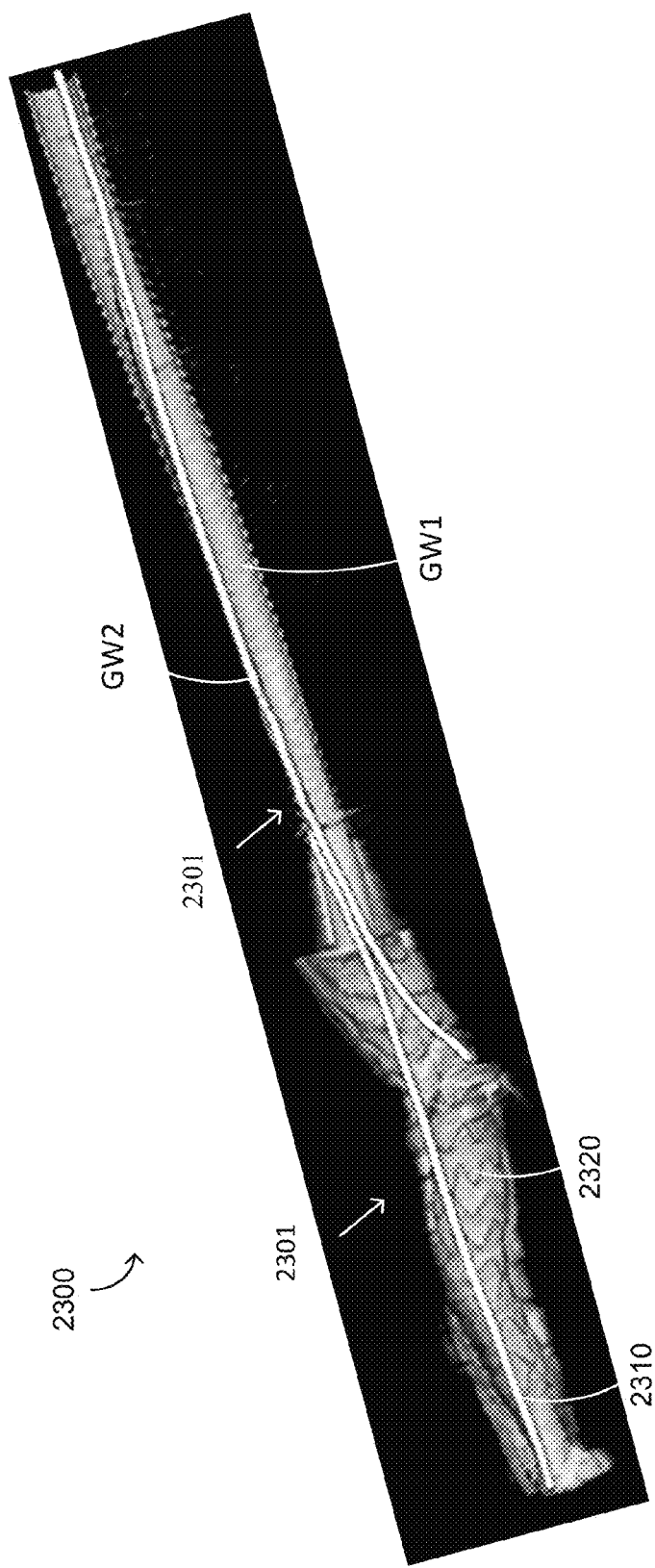
FIG. 23A is a three-dimensional intravascular image with multiple guidewires shown as part of a user interface of a diagnostic system according to an illustrative embodiment of the disclosure.

FIG. 23A is a three-dimensional intravascular image 2300 with two guidewires 2305 and 2310 shown as part of a user interface of a diagnostic system. The image 2300 is a three-dimensional rendered view and is suitable for use on a diagnostic system, such as an intravascular imaging system in a cath lab. The central lumen 2340 of the blood vessel 2301 has two guidewires 2305 (longer GW) and 2310 (shorter GW) passing through it. Various stent struts 2320 are also depicted which are sources of blooming. Struts 2320 appear when imaging the vessel. Detecting the guidewire and its shadows is used to improve stent strut detection because detecting a known shadow, the guide guidewire, reduces false positives. By detecting the guidewire shadow in advance of stent strut processing, the guidewire shadow can be excluded from strut detection. The various methods and processes described herein were applied to generate a displayable representation of the two guidewires after detecting the shadows associated therewith, determining offsets, generating segments, validating segments and generating and validating models/representations of guidewires themselves.

Figure 23B:
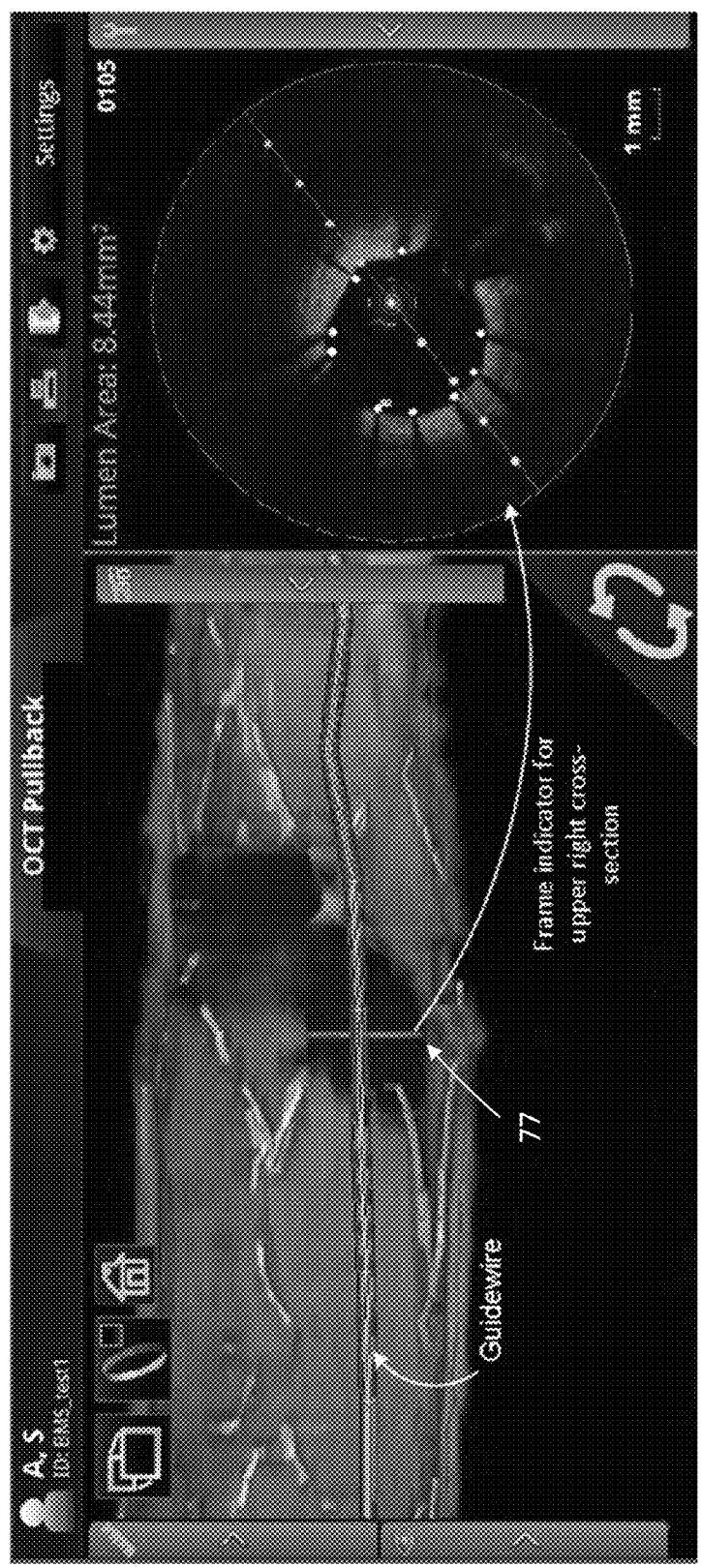
FIG. 23B is a graphic user interface generated using intravascular data that depicts a detected guidewire relative to a lumen as part of a graphic user interface for an intravascular data collection system according to an illustrative embodiment of the disclosure.

FIG. 23B shows an interface display exemplifying a three dimensional, skin and wire-frame view of a deployed stent based on OCT imaging data. This is a three-dimensional representation of an OCT pullback through the blood vessel segment shown. A guidewire has been detected and is labelled in the image and spans the left panel. The guidewire is in the lumen and has various stent struts depicted around it. The detection of the guidewire using various methods described herein such as a carpet view based method and others improve stent detection. Various detected stents are also shown in the image of FIG. 23B. A frame indicator 77 shown as a vertical line appears in the middle of the left panel. This indicator tracks the angled line shown for the upper right cross-sectional view shown in the right panel of FIG. 23B. The lumen area of 8.44 mm² is also shown in the right user interface panel. The user interface display can include the option to display or hide one or more features, such as the skin, guidewire, and/or stent struts of FIGS. 23A and 23B and other user interface features. In addition the color and transparency of the skin can be altered, to make the skin more transparent or more opaque.

Guidewire Model for 3-D Rendering Features

The guidewire method detections contain the information necessary to reconstruct the three dimensional model of the physical guidewires. The model generation is necessary for accurate representation of the guidewire in the 3-D views. This step removes noise and artifacts of the earlier method steps. The specific artifact that this method removes is areas of two guidewire co-location. Guidewire co-location occurs when the wires are overlapping and creating a single shadow. This method attempts to recover the location of the guidewire when earlier method steps do not dissociate this occlusion phenomenon.

Figure 24:
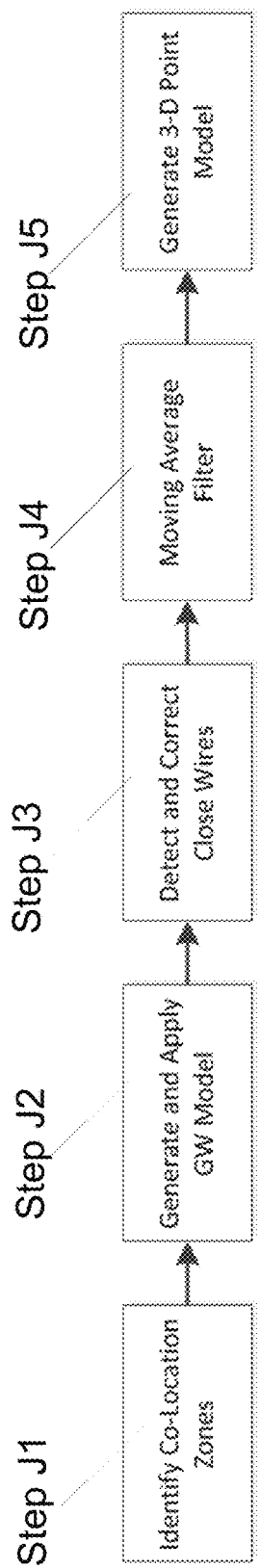
FIG. 24 is a process flow depicting a processing for generating a three-dimensional model of a guidewire according to an illustrative embodiment of the disclosure.
Figure 25:
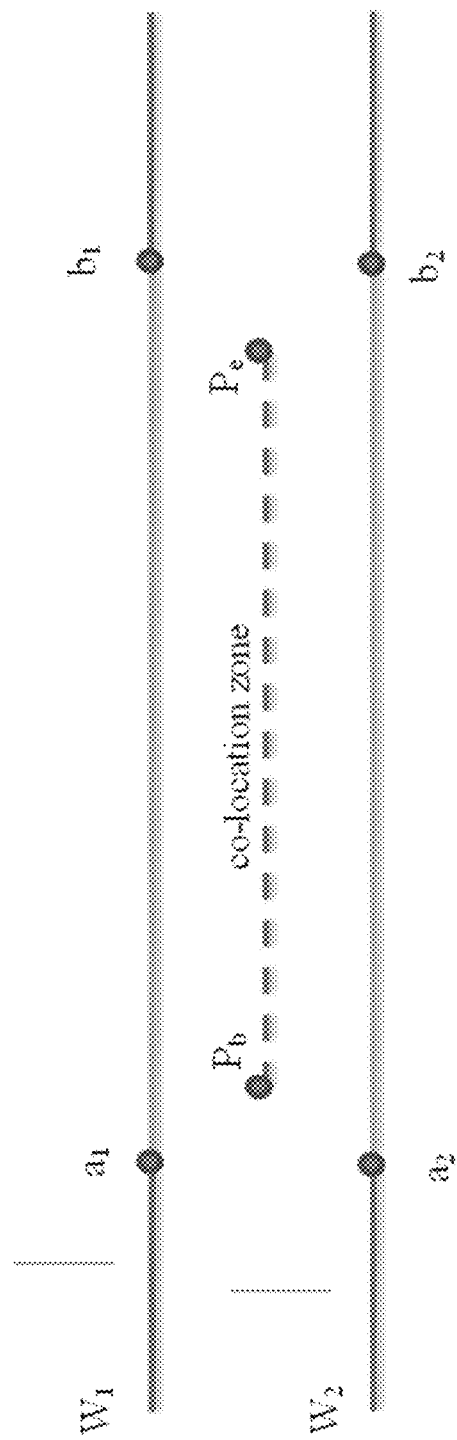
FIG. 25 is a schematic diagram of a guidewire model having a co-location zone according to an illustrative embodiment of the disclosure.

FIG. 24 illustrates the steps of the recovery method. The method identifies the regions of two guidewire co-location and processes each one at a time. The method includes identifying one or more co-location zones Step J1. The method also includes generating and applying a GW model Step J2. Detecting and correcting wires that are close to each other Step J3 is another step of the method. A moving average filter is applied in one embodiment Step J4. In one embodiment, a 3-D point model of the guidewire is generated such that it can be displayed to a user Step J5. FIG. 25 is a schematic diagram of two guidewires W1 and W2. Each wire has two segments a1 to b1 and a2 to b2 respectively. The method shown in FIG. 24 transforms the co-location zone ends ($a_1b_1$ and $a_2b_2$ as shown in FIG. 25) to the origin using the guidewire point ($P_b$ and $P_e$) immediately inside the co-location zone.

In the event candidate wires are detected and selected as the best candidates they may be in close proximity to each other and appear to be co-located. A linear interpolation between $P_b$ and $P_e$ is created to model the offsets needed for disambiguating co-located guidewires. The delta offset is applied to the original co-located points to separate them in 3-D space.

After the co-located points are resolved, another step in the method checks the distance between each guidewire on a per-frame basis. The offset between the guidewires may be below a separation threshold or other metric and used to correct the closeness or proximity of the wires. For example, wires that are determined to be too close to each in space are corrected by translating them along the line that is formed by their points. The amount of offset is calculated based on the physical guidewire dimensions.

After all location corrections, the final step is to smooth the points in order to remove high frequency noise and any artifacts from the earlier detection steps. The points are averaged using a moving average filter Step J4 in FIG. 24. The guidewire model is created and stored in a separate data structure for consumption by the 3-D rendering module.

The methods for guidewire model creation include various substeps and operations as outlined herein. This method identifies the zones where two guidewires are co-located. After the zones are identified, the co-located wires are modeled to preserve endpoint connectivity. In one embodiment, the method checks all or a subset of guidewire points for overlap and corrects the locations if necessary. The method can also perform an average filter of each guidewires' points to remove detection artifacts and noise. The method also generates the model data that is processed and transformed by a 3-D render software module Step J5.

Non-Limiting Software Features and Embodiments for Implementing Interface, Detection and Other Features of Disclosure The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of methods such as algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "searching" or "indicating" or "detecting" or "measuring" or "calculating" or "comparing" or "generating" or "sensing" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer. Various circuits and components thereof can be used to perform some of the data collection and transformation and processing described herein.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description provided herein. In addition, the present disclosure is not described with reference to any particular programming language, and various embodiments may thus be implemented using a variety of programming languages. In one embodiment, the software instructions are configured for operation on a microprocessor or ASIC of an intravascular imaging/data collection system.

Embodiments of the disclosure may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof.

In a typical embodiment of the present disclosure, some or all of the processing of the data collected using an OCT probe, an IVUS probe, other imaging probes, an angiography system, and other imaging and subject monitoring devices and the processor-based system is implemented as a set of computer program instructions that is converted into a computer executable form, stored as such in a computer readable medium, and executed by a microprocessor under the control of an operating system. Thus, user interface instructions and triggers based upon the completion of a pullback or a co-registration request, for example, are transformed into processor understandable instructions suitable for generating OCT data, performing image procession using various and other features and embodiments described above.

In addition, user interface commands, a user query, a system response, transmitted probe data, input data and other data and signal described herein are transformed into processor understandable instructions suitable for responding to user interface selections, controlling a graphical user interface, control and graphic signal processing, displaying cross-sectional information, rendered stents and guidewires and images from other data collection modalities, generating and displaying stents and apposition bars and other intravascular data, displaying OCT, angiography, detecting shadows, detecting peaks, and other data as part of a graphic user interface and other features and embodiments as described above. Data and parameters suitable for display as GUI components or controls, values, or as another representation in a graphical user interface can include without limitation guidewire, apposition bars, user interface panels, masks, stent struts, missing data representations, shadows, angiography representations, three and two dimensional renders and views, and other features as described herein.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing and processing instructions, or various types of data such as angiography data, OCT data, IVUS data, offsets, shadows, pixels, intensity patterns, guidewire segments, linking conditions, mappings of possible linkages, conditions for proximal to distal or other processing orders, OCT scan data, user interface data, control signals, angiography data, user actions, frequencies, interferometer signal data, detected stents, candidate stent struts, FFR data, IVUS data, shadows, pixels, intensity patterns, scores, projections, side branch data, linking rules and constrains, and guidewire data and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

The term "machine-readable medium" or "computer-readable-medium" includes any medium that is capable of storing, encoding or carrying a set of instructions for execution by the machine and that cause the machine to perform any one or more of the methodologies of the present disclosure. While the machine-readable medium is shown in an example embodiment to be a single medium, the term "machine-readable medium" should be taken to include a single medium or multiple media (e.g., a database, one or more centralized or distributed databases and/or associated caches and servers) that store the one or more sets of instructions.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously. The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

Furthermore, whereas particular embodiments of the disclosure have been described herein for the purpose of illustrating the disclosure and not for the purpose of limiting the same, it will be appreciated by those of ordinary skill in the art that numerous variations of the details, materials and arrangement of elements, steps, structures, and/or parts may be made within the principle and scope of the disclosure without departing from the disclosure as described in the claims.

What is claimed is:

1. A method of detecting a guidewire in a blood vessel comprising:
    storing, using an intravascular imaging system, one or more intravascular image datasets of the blood vessel, each intravascular dataset comprising a plurality of scan lines;
    detecting, using one or more guidewire modules of the intravascular imaging system, a guidewire shadow on one or more scan lines of the plurality of scan lines;
    determining a guidewire offset for each guidewire shadow;
    determining on a per frame basis a candidate guidewire detection using one or more guidewire offsets such that a plurality of candidate guidewire detections is generated;
    generating a plurality of candidate guidewire segments from the plurality of candidate guidewire detections;
    removing spurious guidewire segments from the plurality of candidate guidewire segments to generate a set of detected guidewire segments; and
    linking segments from the set of detected guidewire segments, using one or more guidewire modules of the intravascular imaging system, to generate one or more contiguous guidewire representations.

2. The method of claim 1 further comprising displaying a guidewire representation comprising one or more contiguous guidewire representations in a user interface of the intravascular imaging system.

3. The method of claim 1 further comprising
    generating a carpet view from the plurality of scan lines; and
    binarizing the carpet view to generate a binary carpet view mask;
    wherein the step of removing spurious guidewire segments includes scoring candidate guidewire segments based on intersection of the candidate segments with "on" regions in the binary carpet view mask.

4. The method of claim 1 further comprising
    generating a mapping of all possible detection linkages from the plurality of candidate guidewire detections, and using the segment mapping to link the detections into contiguous guidewire representations.

5. The method of claim 1 wherein one or more of the steps of:
    detecting a guidewire shadow on one or more scan lines of the plurality of scan lines;
    determining a guidewire offset for each guidewire shadow; and
    determining on a per frame basis a candidate guidewire detection is performed using a single-frame processing implementation.

6. The method of claim 1 wherein one or more of the steps of:
    generating a plurality of candidate guidewire segments;
    removing spurious guidewire segments; and
    forming guidewire representations from the set of detected guidewire segments are performed using a multi-frame processing implementation.

7. The method of claim 1 wherein segment linking further comprises:
    linking a detection from a distal frame to an existing segment if a distance metric between a tail of the segment and a new detection is less than a threshold; and
    linking a detection from a next most distal frame to an existing segment if an extrapolated location of that segment within the frame lies within a narrow distance of the detection.

8. The method of claim 1 further comprising providing interpolated detections when segments are linked to detections that lie on frames crossing over one or more frames on which there are no detection.

9. The method of claim 1 wherein segments are filtered using a set of exclusion rules to remove segments that have probability of less than about 0.5 of corresponding to an actual guidewire.

10. The method of claim 1 wherein distinct segments are bounded by one or more of a split and a merge in which a parent segment is linked to two child segments (for a split) or two parents connect to a single child segment (for a merge).

11. The method of claim 1 in which segments are linked based upon occurrence of one or more conditions selected from the group consisting of
    each unique segment has at least one corresponding wire associated with it,
    when a segment splits in two, a new wire is created,
    when segments merge, a resulting segment is associated with multiple wires associated with parent segments,
    duplicate wires are eliminated after linking, and
    wires travelling along common segments are disambiguated for visualization purposes by translating detections on common segments away from each other so that rendered guidewires do not overlap in 3-D space.

12. The method of claim 1 further comprising displaying a representation of the guidewire relative to a representation of a lumen of a blood vessel.

13. A programmable processor-based computing device of an intravascular imaging system for detecting one or more guidewires in a blood vessel, the programmable processor-based computing device comprising:
    one or more data access channels to receive intravascular imaging data;
    a processor and associated memory in electrical communication with the one or more data access channels, wherein the processor is programmed to:
    store, using an intravascular imaging system, one or more intravascular image datasets of the blood vessel, each intravascular dataset comprising a plurality of scan lines;
    detect, using one or more guidewire modules of the intravascular imaging system, a guidewire shadow on one or more scan lines of the plurality of scan lines;

determine a guidewire offset for each guidewire shadow;
determine on a per frame basis a candidate guidewire detection using one or more guidewire offsets such that a plurality of candidate guidewire detections is generated;
generate a plurality of candidate guidewire segments from the plurality of candidate guidewire detections;
remove spurious guidewire segments from the plurality of candidate guidewire segments to generate a set of detected guidewire segments; and
link segments from the set of detected guidewire segments, using one or more guidewire modules of the intravascular imaging system, to generate one or more contiguous guidewire representations.

14. The programmable processor-based computing device of claim 13, wherein the processor is further programmed to display a guidewire representation comprising one or more contiguous guidewire representations in a user interface of the intravascular imaging system.

15. The programmable processor-based computing device of claim 13, wherein the processor is further programmed to
generating a carpet view from the plurality of scan lines; and
binarizing the carpet view to generate a binary carpet view mask;
wherein the step of removing spurious guidewire segments includes scoring candidate guidewire segments based on intersection of the candidate segments with "on" regions in the binary carpet view mask.

16. The programmable processor-based computing device of claim 13, wherein the processor is further programmed to generate a mapping of all possible detection linkages from the plurality of candidate guidewire detections, and using the segment mapping to link the detections into contiguous guidewire representations.

17. The programmable processor-based computing device of claim 13, wherein one or more of:
detect a guidewire shadow on one or more scan lines of the plurality of scan lines;
determine a guidewire offset for each guidewire shadow; and
determine on a per frame basis a candidate guidewire detection is performed using a single-frame processing instructions.

18. The programmable processor-based computing device of claim 13, wherein one or more of:
generating a plurality of candidate guidewire segments;
removing spurious guidewire segments; and
forming guidewire representations from the set of detected guidewire segments are performed using a multi-frame processing implementation.

19. The programmable processor-based computing device of claim 13 wherein segment linking further comprises:
linking a detection from a distal frame to an existing segment if a distance metric between a tail of the segment and a new detection is less than a threshold; and
linking a detection from a next most distal frame to an existing segment if an extrapolated location of that segment within the frame lies within a narrow distance of the detection.

20. The programmable processor-based computing device of claim 13, wherein the processor is further programmed to provide interpolated detections when segments are linked to detections that lie on frames crossing over one or more frames on which there are no detection.

21. The programmable processor-based computing device of claim 13, wherein segments are filtered using a set of exclusion rules to remove segments that have probability of less than about 0.5 of corresponding to an actual guidewire.

22. The programmable processor-based computing device of claim 13, wherein distinct segments are bounded by one or more of a split and a merge in which a parent segment is linked to two child segments (for a split) or two parents connect to a single child segment (for a merge).

23. The programmable processor-based computing device of claim 13, wherein segments are linked based upon occurrence of one or more conditions selected from the group consisting of
each unique segment has at least one corresponding wire associated with it;
when a segments splits in two, a new wire is created;
when segments merge, a resulting segment is associated with multiple wires associated with the parent segments;
duplicate wires are eliminated after linking; and
wires travelling along common segments are disambiguated for visualization purposes by translating the detections on the common segments away from each other so that rendered guidewires do not overlap in 3-D space.

* * * * *